United States Patent
Walsh

(10) Patent No.: US 7,948,631 B2
(45) Date of Patent: May 24, 2011

(54) METHOD AND APPARATUS FOR USING MULTIPLE RELATIVE REFLECTANCE MEASUREMENTS TO DETERMINE PROPERTIES OF A SAMPLE USING VACUUM ULTRA VIOLET WAVELENGTHS

(75) Inventor: Phillip Walsh, Austin, TX (US)

(73) Assignee: Jordan Valley Semiconductors Ltd., Migdal Haemer (IL)

( * ) Notice: Subject to any disclaimer, the term of this patent is extended or adjusted under 35 U.S.C. 154(b) by 0 days.

(21) Appl. No.: 12/592,641

(22) Filed: Nov. 30, 2009

(65) Prior Publication Data

US 2010/0171959 A1      Jul. 8, 2010

Related U.S. Application Data

(63) Continuation of application No. 12/072,878, filed on Feb. 28, 2008, now abandoned.

(51) Int. Cl.
*G01N 21/55* (2006.01)
(52) U.S. Cl. ......................... 356/445; 356/448
(58) Field of Classification Search .......... 356/445–447, 356/600–601, 237.2, 630–632, 369, 503–504; 250/559.27–559.28, 559.39, 559.41; 438/14, 438/16; 216/85, 88, 89
See application file for complete search history.

(56) References Cited

U.S. PATENT DOCUMENTS

| | | | |
|---|---|---|---|
| 3,091,154 A | 5/1963 | Hall | |
| 3,160,752 A | 12/1964 | Bennett | |
| 3,572,951 A | 3/1971 | Rothwarf et al. | |
| 3,751,643 A | 8/1973 | Dill et al. | |
| 3,825,347 A | 7/1974 | Kaiser | |
| 4,029,419 A | 6/1977 | Schumann et al. | |
| 4,040,750 A | 8/1977 | Zwiener | |
| 4,368,983 A | 1/1983 | Bennett | |
| 4,645,349 A | 2/1987 | Tabata | |
| 4,729,657 A | 3/1988 | Cooper et al. | |

(Continued)

FOREIGN PATENT DOCUMENTS

CN      2430682 Y      5/2001

(Continued)

OTHER PUBLICATIONS

U.S. Appl. No. 12/590,151 Official Action dated Jun. 25, 2010.

(Continued)

*Primary Examiner* — Gregory J Toatley
*Assistant Examiner* — Tri T Ton
(74) *Attorney, Agent, or Firm* — D. Kligler I.P. Services Ltd

(57) ABSTRACT

A method and apparatus is disclosed for measuring properties of an unknown sample. A reflectometer and one or more reference pieces is provided. A set of data is collected from the unknown sample and a combination of the reference pieces. A combination of the sample and reference piece data independent of incident intensity is used to determine a property of the unknown sample without calibrating incident reflectometer intensity. The method and apparatus disclosed can measure properties of thin films or scattering structures on semiconductor work pieces. In one embodiment the reflectometer utilizes vacuum ultraviolet (VUV) wavelength reflectometry. Multiple relative reflectance measurements are used to overcome effects of the inevitable contamination buildup that occurs when using optical systems in the VUV region. While advantageous for VUV wavelengths, the method described herein is generally applicable to any wavelength range, and is advantageous in situations where stable reference samples are not available.

39 Claims, 16 Drawing Sheets

U.S. PATENT DOCUMENTS

| | | | |
|---|---|---|---|
| 4,837,603 A | 6/1989 | Hayashi |
| 4,899,055 A | 2/1990 | Adams |
| 4,984,894 A | 1/1991 | Kondo |
| 5,042,949 A | 8/1991 | Greenberg et al. |
| 5,045,704 A | 9/1991 | Coates |
| 5,120,966 A | 6/1992 | Kondo |
| 5,128,549 A | 7/1992 | Kaye |
| 5,182,618 A | 1/1993 | Heinonen |
| 5,241,366 A | 8/1993 | Bevis et al. |
| 5,251,006 A | 10/1993 | Hongis et al. |
| 5,357,448 A | 10/1994 | Stanford |
| RE34,783 E | 11/1994 | Coates |
| 5,388,909 A | 2/1995 | Johnson et al. |
| 5,440,141 A | 8/1995 | Horie |
| 5,452,091 A | 9/1995 | Johnson |
| 5,486,701 A | 1/1996 | Norton et al. |
| 5,493,401 A | 2/1996 | Horie et al. |
| 5,581,350 A | 12/1996 | Chen et al. |
| 5,607,800 A | 3/1997 | Ziger |
| 5,608,526 A | 3/1997 | Piwonka-Corle et al. |
| 5,686,993 A | 11/1997 | Kokubo et al. |
| 5,747,813 A | 5/1998 | Norton et al. |
| 5,754,296 A | 5/1998 | Law |
| 5,771,094 A | 6/1998 | Carter |
| 5,777,733 A | 7/1998 | Radziuk |
| 5,781,304 A | 7/1998 | Kotidis et al. |
| 5,784,167 A | 7/1998 | Ho |
| 5,798,837 A | 8/1998 | Aspnes et al. |
| 5,805,285 A | 9/1998 | Jons et al. |
| 5,867,276 A | 2/1999 | McNeil et al. |
| 5,880,831 A | 3/1999 | Buermann et al. |
| 5,900,939 A | 5/1999 | Aspnes et al. |
| 5,903,351 A | 5/1999 | Jeong et al. |
| 5,917,594 A | 6/1999 | Norton |
| 5,991,022 A | 11/1999 | Buermann et al. |
| 6,052,401 A | 4/2000 | Wieser et al. |
| 6,091,485 A | 7/2000 | Li et al. |
| 6,122,052 A | 9/2000 | Barnes et al. |
| 6,128,085 A | 10/2000 | Buermann et al. |
| 6,129,807 A | 10/2000 | Grimbergen et al. |
| 6,181,427 B1 | 1/2001 | Yarussi et al. |
| 6,184,529 B1 | 2/2001 | Contini |
| 6,184,984 B1 | 2/2001 | Lee |
| 6,226,086 B1 | 5/2001 | Hoolbrook et al. |
| 6,261,853 B1 | 7/2001 | Howell et al. |
| 6,265,033 B1 | 7/2001 | Hilliard et al. |
| 6,275,292 B1 | 8/2001 | Thakur et al. |
| 6,278,519 B1 | 8/2001 | Rosencwaig et al. |
| 6,297,880 B1 | 10/2001 | Rosencwaig et al. |
| 6,304,326 B1 | 10/2001 | Aspnes et al. |
| 6,313,466 B1 | 11/2001 | Olsen et al. |
| 6,340,602 B1 | 1/2002 | Johnson et al. |
| 6,361,646 B1 | 3/2002 | Bibby, Jr. et al. |
| 6,392,756 B1 | 5/2002 | Li et al. |
| 6,411,385 B2 | 6/2002 | Aspnes et al. |
| 6,414,302 B1 | 7/2002 | Freeouf |
| 6,417,921 B2 | 7/2002 | Rosencwaig et al. |
| 6,433,878 B1 | 8/2002 | Niu et al. |
| 6,453,006 B1 | 9/2002 | Koppel |
| 6,485,872 B1 | 11/2002 | Rosenthal et al. |
| 6,525,829 B1 | 2/2003 | Powell et al. |
| 6,549,279 B2 | 4/2003 | Adams et al. |
| 6,556,303 B1 | 4/2003 | Rangaran et al. |
| 6,572,951 B2 | 6/2003 | Hasegawa et al. |
| 6,580,510 B2 | 6/2003 | Nawracala |
| 6,590,656 B2 | 7/2003 | Yu et al. |
| 6,608,690 B2 | 8/2003 | Niu et al. |
| 6,630,673 B2 | 10/2003 | Khalil et al. |
| 6,630,996 B2 | 10/2003 | Rao et al. |
| 6,633,831 B2 | 10/2003 | Nikoonahad |
| 6,643,354 B2 | 11/2003 | Koppel |
| 6,657,737 B2 | 12/2003 | Kimba et al. |
| 6,665,075 B2 | 12/2003 | Mittleman et al. |
| 6,710,865 B2 | 3/2004 | Forouhi et al. |
| 6,713,775 B2 | 3/2004 | Chelvayohan et al. |
| 6,721,052 B2 | 4/2004 | Zhao et al. |
| 6,734,968 B1 | 5/2004 | Wang et al. |
| 6,765,676 B1 | 7/2004 | Buermann |
| 6,768,785 B2 | 7/2004 | Koppel |
| 6,801,309 B1 | 10/2004 | Nelson |
| 6,879,395 B2 | 4/2005 | Oka et al. |
| 6,891,626 B2 | 5/2005 | Niu et al. |
| 6,897,456 B2 | 5/2005 | Hasegawa et al. |
| 6,897,807 B2 | 5/2005 | Kishigami et al. |
| 6,934,025 B2 | 8/2005 | Opsal et al. |
| 6,987,832 B2 | 1/2006 | Koppel |
| 7,026,165 B2 | 4/2006 | Degrandpre |
| 7,026,626 B2 | 4/2006 | Harrison |
| 7,061,614 B2 | 6/2006 | Wang et al. |
| 7,067,818 B2 | 6/2006 | Harrison |
| 7,072,050 B2 | 7/2006 | Kimba et al. |
| 7,126,131 B2 | 10/2006 | Harrison |
| 7,189,973 B2 | 3/2007 | Harrison |
| 7,224,471 B2 | 5/2007 | Bischoff et al. |
| 7,271,394 B2 | 9/2007 | Harrison |
| 7,282,703 B2 | 10/2007 | Walsh et al. |
| 7,394,551 B2 | 7/2008 | Harrison |
| 7,485,869 B2 | 2/2009 | Harrison et al. |
| 7,579,601 B2 | 8/2009 | Harrison |
| 7,643,666 B2 | 1/2010 | Setija et al. |
| 7,684,037 B2 | 3/2010 | Harrison et al. |
| 2001/0055118 A1 | 12/2001 | Nawracala |
| 2002/0030826 A1 | 3/2002 | Chalmers et al. |
| 2002/0110218 A1 | 8/2002 | Koppel |
| 2002/0149774 A1 | 10/2002 | McAninch |
| 2002/0154302 A1 | 10/2002 | Rosencwaig |
| 2002/0179864 A1 | 12/2002 | Fielden |
| 2002/0179867 A1 | 12/2002 | Fielden |
| 2002/0180961 A1 | 12/2002 | Wack |
| 2002/0180985 A1 | 12/2002 | Wack |
| 2002/0180986 A1 | 12/2002 | Nikoonahad |
| 2002/0182760 A1 | 12/2002 | Wack |
| 2002/0190207 A1 | 12/2002 | Levy |
| 2003/0011786 A1 | 1/2003 | Levy |
| 2003/0071996 A1 | 4/2003 | Wang et al. |
| 2004/0032593 A1 | 2/2004 | Venugopal |
| 2004/0052330 A1 | 3/2004 | Koppel |
| 2004/0150820 A1 | 8/2004 | Nikoonahad et al. |
| 2004/0218717 A1 | 11/2004 | Koppel |
| 2005/0002037 A1 | 1/2005 | Harrison |
| 2005/0036143 A1 | 2/2005 | Huang |
| 2006/0001885 A1 * | 1/2006 | Hertzsch et al. ............ 356/446 |
| 2007/0030488 A1 | 2/2007 | Harrison |
| 2007/0181793 A1 | 8/2007 | Harrison |
| 2007/0181795 A1 | 8/2007 | Walsh et al. |
| 2007/0182970 A1 | 8/2007 | Harrison |
| 2007/0215801 A1 | 9/2007 | Walsh et al. |
| 2008/0042071 A1 | 2/2008 | Harrison |
| 2008/0246951 A1 | 10/2008 | Walsh et al. |
| 2009/0002711 A1 | 1/2009 | Harrison |
| 2009/0248074 A1 | 10/2009 | Kliegman |
| 2010/0051822 A1 | 3/2010 | Harrison |

FOREIGN PATENT DOCUMENTS

| | | |
|---|---|---|
| JP | 10160572 A | 6/1998 |
| JP | 2003202266 A | 7/2003 |
| JP | 2003232681 A | 8/2003 |
| WO | 9902970 A1 | 1/1999 |

OTHER PUBLICATIONS

US Re-Examination Application # 90/009,409 Official Action dated Jun. 18, 2010.
Chinese Patent Application No. 200480027513.6 Official Action dated Jul. 18, 2008.
US Re-Examination Application # 90/009,320 Official Action dated Sep. 25, 2009, and Notice of Intent to Issue Re-Exam Certificate dated Jun. 23, 2010.
International Application PCT/US2007/010003 Search Report issued Dec. 17, 2008.
U.S. Appl. No. 10/930,339 Official Action dated Sep. 29, 2009.
U.S. Appl. No. 10/930,339 Official Action dated Jan. 18, 2007.
U.S. Appl. No. 10/930,339 Official Action dated Sep. 6, 2007.
U.S. Appl. No. 10/930,339 Official Action dated Apr. 18, 2008.
U.S. Appl. No. 10/930,339 Official Action dated Nov. 13, 2008.
Hurst et al., U.S. Appl. No. 12/454,837 "Automated Calibration Methodology for VUV Metrology System" filed May 22, 2009.

Das et al., "Image Evaluation of the High-Resolution VUV Spectrometer at SURF II by Ray Tracing", Journal of Research of the National Institute of Standards and Technology, vol. 103, No. 5, pp. 483-495, Sep.-Oct. 1998.

Request for Ex Parte Reexamination for US Patent # 7,067,818 filed Feb. 11, 2009.

Request for Ex Parte Reexamination for US Patent # 7,067,818 filed Feb. 12, 2010.

Request for Ex Parte Reexamination for US Patent # 7,026,626 filed Nov. 7, 2008.

International Application PCT/US2004/030859 Search Report issued Feb. 24, 2005.

Rivas, "Optical Characterization of Hafnium-Based High-K Dielectric Films Using Vacuum Ultraviolet Reflectometry", XV International Conference on Vacuum Ultraviolet Radiation Physics, 2007, 6 pgs.

Bloomstein et al., "Contamination Rates of Optical Surface At 157NM in the Presence of Hydrocarbon Impurities", Optical Microlithography XV, Proceedings of the SPIE, vol. 4691, 2002, 15 pgs.

Okoroanyanwu et al., "Contamination Monitoring and Control on ASML MS-VII 157nm Exposure Tool", Optical Microlithography XVII, Proceedings of the SPIE, vol. 5377, 2004, 13 pgs.

"Optical Characterization of Molecular Contaminant Films" Photonics Tech Briefs, 2007, 2 pgs.

Aspnes, "The Accurate Determination of Optical Properties by Ellipsometry", Handbook of Optical Constants of Solids, vol. 1, ed. D, Academic Press, 1998, 5 pgs.

Press et al., "Numerical Recipes in C" The Art of Scientific Computing, Second Edition, 1992, 15.5 Nonlinear Models, pp. 681-688.

Jellison et al, "Parameterization of the Optical Functions of Amorphous Materials in the Interband Region", Applied Physics Letter, vol. 69, 1996, 3 pgs.

Jellison et al, "Erratum: Parameterization of the Optical Functions of Amorphous Materials in the Interband Region", Applied Physics Letter, vol. 69, 1996, 1 pg.

Field et al., "Method of Using the Reflectance Ratios of Different Angles of Incidence for the Determination of Optical Constants", Applied Optics, vol. 10, No. 6, Jun. 1971, 4 pgs.

Hunter et al., "Thickness of Absorbing Films Necessary to Measure Their Optical Constants Using the Reflectance-Vs-Angle-Of-Incidence Method", Journal of the Optical Society of America, vol. 64, No. 4, Apr. 1874, 5 pgs.

Hunter et al., "Journal of the Optical Society of America", Optical Society of America, vol. 55, No. 10, Part 1, Oct. 1965, 8 pgs.

Rubloff, "Surface Reflectance Spectroscopy System", Technical Disclosure, Ip.com, www.ip.com, May 1, 1977, 5 pgs.

McPherson Product Brochure "Reflectometer for Sample Analysis," McPherson, Inc., Massachusetts, Published Prior to Sep. 23, 2003, 1-2 pps.

McPherson Product Brochure "Spectral Reflectometer," McPherson, Inc., Massachusetts, Nov. 12, 2001, 1 pg.

McPherson Product Brochure "VUVaS Spectrophotometer for 115 nm to >380 nm," McPherson, Inc., Massachusetts, Published Prior to Sep. 23, 2003, 1-4 pps.

McPherson Product Brochure "VUVaS Spectrophotometers, Made to Measure 115-380 nm," McPherson, Inc., Massachusetts, Published Prior to Sep. 23, 2003, 1-8 pps.

Acton Research Product Brochure "Acton Research Purged CAMS Optical Measurement System," Acton Research Corporation, Massachusetts, Published Prior to Sep. 23, 2003, 1-2 pps.

"The Thin Film tool for next generation lithography at 157nm," Web page from http://www.sopra-sa.com, Sopra, Printed From Internet On Feb. 19, 2002, 1pg.

"SE and GXR combined on the same instrument," Web page from http://www.sopra-sa.com, Sopra, Printed From Internet on Feb. 19, 2002, 1pg.

"The ideal Thin Film characterization unit for Development and Pilot Line environment," Web page from http://www.sopra-sa.com, Sopra, Printed From Internet on Feb. 19, 2002, 1 pg.

"VUV-VASE™, The Award Winning VUV-VASE™ is the latest addition to our line of Spectroscopic Ellipsometers," Web pages from http://www.jawoolam.com, J.A. Woollam Company, Nebraska, Printed From Internet on Nov. 5, 2002, 1-2 pps.

"Vaccum UV Spectroscopic Ellipsometers," Web pages from http://www.sentech.de, Sentech Instruments, Printed From Internet on Feb. 20, 2002, 1-3 pps.

Copending Application, Walsh, "Method And Apparatus For Using Multiple Relative Reflectance Measurements To Determine Properties Of A Sample Using Vacuum Ultra Violet Wavelengths", U.S. Appl. No. 12/072,878, filed Feb. 28, 2008, 43 pgs.

Japanese Patent Application # 528098/06 Official Action dated Jun. 15, 2010 (including English translation).

U.S. Appl. No. 12/876,242 Official Action dated Nov. 19, 2010.

* cited by examiner

METHOD AND APPARATUS FOR USING MULTIPLE RELATIVE REFLECTANCE MEASUREMENTS TO DETERMINE PROPERTIES OF A SAMPLE USING VACUUM ULTRA VIOLET WAVELENGTHS

CROSS-REFERENCE TO RELATED APPLICATIONS

This application is a continuation of U.S. patent application Ser. No. 12/072,878 filed on Feb. 28, 2008 now abandoned.

TECHNICAL FIELD

A method and apparatus for using reflectometry for measuring properties of thin films or scattering structures on semiconductor work-pieces is disclosed. The techniques described herein include a method for using multiple relative reflectance measurements to overcome effects of contamination buildup. While the methods are particularly advantageous for vacuum ultraviolet (VUV) wavelengths, the methods are generally applicable to any wavelength range, and are advantageous in situations where stable reference samples are not available.

BACKGROUND

The techniques described herein relate to the field of optical metrology. Optical methods for control of thin film properties in semiconductor (and other) device manufacturing environments have become widely accepted. Particular advantages of using optical metrology include a high measurement throughput and the fact that optical measurements are typically nondestructive.

The most common optical metrology techniques are reflectometry and ellipsometry. Ellipsometry is generally regarded as consisting of a "richer" dataset, including a measurement of two quantities per wavelength/incident angle. On the other hand, reflectometers are more robust due to less complex hardware configuration, have faster measurements, and typically have a smaller footprint. Generally speaking, if both technologies are capable of solving a given metrology problem, the reflectometer is a more cost effective choice for a high-volume production environment.

Semiconductor device manufacturing is characterized by continually decreasing feature sizes. For example, in integrated circuit (IC) devices, the shrinking of the gate length has caused a corresponding decrease in the gate dielectric thickness to the order of 1 nm. Consequently, an important manufacturing issue is control of properties of ultra-thin films such as for example silicon oxynitrides or hafnium silicate films. Usually, control of film thickness is of primary importance, but control of film composition can be equally important, since both properties influence the final IC device performance.

This shrinking of device dimensions is where vacuum ultra-violet wavelength metrology comes in. It is well-known that a decrease in incident wavelength enhances sensitivity of the detected signal to minute changes in samples properties. An example is reflectance of ~1-2 nm silicon dioxide films on silicon substrates. FIGS. 1A and 1B compare simulated reflectances of 10 Å SiO$_2$/Si film (plot 101), 11 Å SiO$_2$/Si film (plot 102), and 12 Å SiO$_2$/Si film (plot 103). Changes in film thickness are only detectable in the deep-ultra violet (DUV) and VUV regions, are more resolved the shorter the wavelength, and are undetectable in the visible wavelength regions. FIG. 1A shows a reflectance range of 30% to 80% and a wavelength range of 120 nm to 1000 nm, while FIG. 1B is an expanded version of a portion of FIG. 1A, with a reflectance range of 45% to 70% and a wavelength range of 120 nm to 220 nm. The differences between the reflectances of plots 101, 102 and 103 are more apparent in FIG. 1B.

Somewhat less known in the art is the ability to distinguish the effects of multiple parameters on the detected spectrum as the incident wavelength decreases below DUV regions. The ability to determine changes in film thickness and composition independently is enhanced in the VUV region, where many films exhibit very rich absorption spectra. Thus, using only DUV wavelengths, it may be possible to distinguish thickness or composition changes in an ultra-thin film, but not simultaneously. To do this with a reflectometer, one must move to VUV wavelengths, as illustrated in "Optical characterization of hafnium-based high-k dielectric films using vacuum ultraviolet reflectometry" (C. Rivas, XV International Conference on Vacuum Ultraviolet Radiation Physics, published 2007) for the case of Hf$_x$Si$_{1-x}$O$_2$, or in FIGS. 2A-C for silicon oxynitride (SiON). FIGS. 2A, 2B, and 2C compare reflectances for three SiON film cases: 30 Å thick, 15% nitride component (plot 201), 31 Å thick 15% nitride component (plot 202), and 30 Å thick, 17% nitride component (plot 203). FIG. 2A shows a reflectance range of 10% to 80%, and a wavelength range of 120 nm to 1000 nm. FIG. 2B shows an expanded version of a portion of FIG. 2A, with a reflectance range of 15% to 55%, and a wavelength range of 120 nm to 160 nm. FIG. 2C shows a second expanded version of a portion of FIG. 2A, with a reflectance range of 60% to 70%, and a wavelength of 180 nm to 300 nm. FIG. 2B shows that VUV reflectance can be used to distinguish all three films. FIG. 2C illustrates how DUV reflectance can distinguish the first film from the other two, but cannot distinguish the change of 1 Å thickness from a change of 2% nitride component. In addition, the variety and richness of absorption structure in the VUV for many dielectric materials means that reflectance data often contains as much as or even more information than ellipsometric data, even when the data is taken from the same wavelength region. FIG. 2D shows the optical parameters, n and k, for the oxide and nitride components of the oxynitride film. In FIG. 2D, n SiO2 plot 206, k SiO2 plot 207, n Si3N4 plot 208, and k Si3N4 plot 209 are shown. The large difference in absorption properties (as indicated in the k spectra) in the VUV regions is a key enabler for VUV reflectometry.

Consequently, a VUV reflectometer has been disclosed in U.S. Pat. Nos. 7,026,626, 7,067,818, 7,126,131, and 7,271,394, the disclosures of which are expressly incorporated herein by reference in their entirety. This reflectometer has overcome the difficulties involved with VUV operation, and in particular incorporates an inert gas environment, as well as a real-time reference procedure to enhance stability.

A formidable obstacle to stable, reliable metrology at VUV wavelengths is a buildup of contaminants on optical surfaces during operation. This contaminant buildup is generally characteristic of all optical systems operating in the VUV region, and has also been observed in initial 157 nm lithographic systems, as seen in "Contamination rates of optical surface at 157 nm in the presence of hydrocarbon impurities", (T. M. Bloomstein, V. Liverman, M. Rothschild, S. T. Palmacci, D. E. Hardy, and J. H. C. Sedlacek, Optical Microlithography XV, Proceedings of the SPIE, Vol. 4691, p. 709, published 2002) and "Contamination monitoring and control on ASML MS-VII 157 nm exposure tool", (U. Okoroanyanwu, R. Gronheid, J. Coenen, J. Hermans, K. Ronse, Optical Microlithography XVII, Proceedings of the SPIE, Vol. 5377, p. 1695, published 2004), as well as space-based VUV experiments, such as "Optical Characterization of Molecular Contaminant Films", (Photonics Tech Briefs, January 2007). For fab production environments, the contaminant is thought to involve a photodeposition process as VUV light interacts with siloxanes, hydrocarbons, and other compounds common in fab environments.

One method for calibrating a VUV reflectometer system that takes into account contaminant buildup has been disclosed in U.S. patent application Ser. No. 10/930,339 filed on Aug. 31, 2004, Ser. No. 11/418,827 filed May 5, 2006 (now U.S. Pat. No. 7,282,703), Ser. No. 11/418,846 filed May 5, 2006, and Ser. No. 11/789,686, filed on Apr. 25, 2007, which are all expressly incorporated herein by reference in their entirety. This method involves using a reflectance ratio, which is independent of incident system intensity, to measure properties of contaminant layers on the calibration samples. The measured contaminant layer properties are used to calculate the reflectance spectra of the calibration samples, which enables the determination of the incident intensity from the intensity reflected from the calibration sample. Once the incident intensity is known, an absolute reflectance can be measured for any subsequent sample.

SUMMARY

The techniques disclosed herein provide an alternate method (distinct from the above mentioned U.S. patent application Ser. Nos. 10/930,339, 11/418,827, 11/418,846, and 11/789,686) of measurement using reflectometry that bypasses system calibration and utilizes multiple reflectance ratios, independent of system intensity, to simultaneously measure the properties of an unknown sample and the contaminant buildup on reference surfaces. The method can provide better long-term measurement stability for some ultra-thin film measurements. In one embodiment the reflectometer utilizes vacuum ultraviolet (VUV) wavelength reflectometry.

In one embodiment a method of measuring properties of an unknown sample is provided. The method may comprise providing a reflectometer and at least one reference sample, wherein the at least one reference sample is unstable under conditions in which the reflectometer is operated, collecting a set of data from the unknown sample and at least one reference sample, and utilizing a combination of the unknown sample and reference sample data that is independent of incident intensity to determine a property of the unknown sample, without calibrating incident reflectometer intensity.

In another embodiment a system for measuring properties of an unknown sample is provided. The system may comprise at least one reference sample and a reflectometer, configured for collecting a set of data from the unknown sample and the at least one reference sample wherein the at least one reference sample is unstable under conditions in which the reflectometer is operated. The system may also comprise a computer operating a software routine configured to utilize a combination of the unknown sample and reference sample data that is independent of incident intensity to determine a property of the unknown sample, without calibrating incident reflectometer intensity.

In another embodiment a system for measuring properties of an unknown sample, may comprise at least one reference sample and a reflectometer configured for collecting a set of data from the unknown sample and the at least one reference sample wherein the at least one reference sample is unstable under conditions in which the reflectometer is operated. The system may further comprise a computer operating a software routine that selectably operates in at least one of a plurality of measurement modes, the plurality of measurement modes including at least a first measurement mode and a second measurement mode. The first measurement mode is configured to utilize a combination of the unknown sample and reference sample data that is independent of incident intensity to determine a property of the unknown sample, without calibrating incident reflectometer intensity. The second measurement mode is configured to utilize the reference sample data in a manner that is independent of incident intensity to determine one or more properties of one or more reference pieces, thereby determining the incident intensity of the reflectometer, after which reflectance of unknown samples may be determined.

In yet another embodiment, a method of measuring properties of an unknown sample, may comprising providing a reflectometer and at least one reference sample, wherein the at least one reference sample is unstable under conditions in which the reflectometer is operated and collecting a set of data from the unknown sample and at least one reference sample. The method further comprises selectably operating the system in at least one of a plurality of measurement modes, the plurality of measurement modes including at least a first measurement mode and a second measurement mode. The first measurement mode is configured to utilize a combination of the unknown sample and reference sample data that is independent of incident intensity to determine a property of the unknown sample, without calibrating incident reflectometer intensity. The second measurement mode is configured to utilize the reference sample data in a manner that is independent of incident intensity to determine one or more properties of one or more reference pieces, thereby determining the incident intensity of the reflectometer, after which reflectance of unknown samples may be determined.

As described below, other features and variations can be implemented, if desired, and a related method can be utilized, as well.

DESCRIPTION OF THE DRAWINGS

It is noted that the appended drawings illustrate only exemplary embodiments of the techniques disclosed herein and are, therefore, not to be considered limiting of its scope, for the techniques disclosed herein may admit to other equally effective embodiments.

DETAILED DESCRIPTION

Figure 1A:
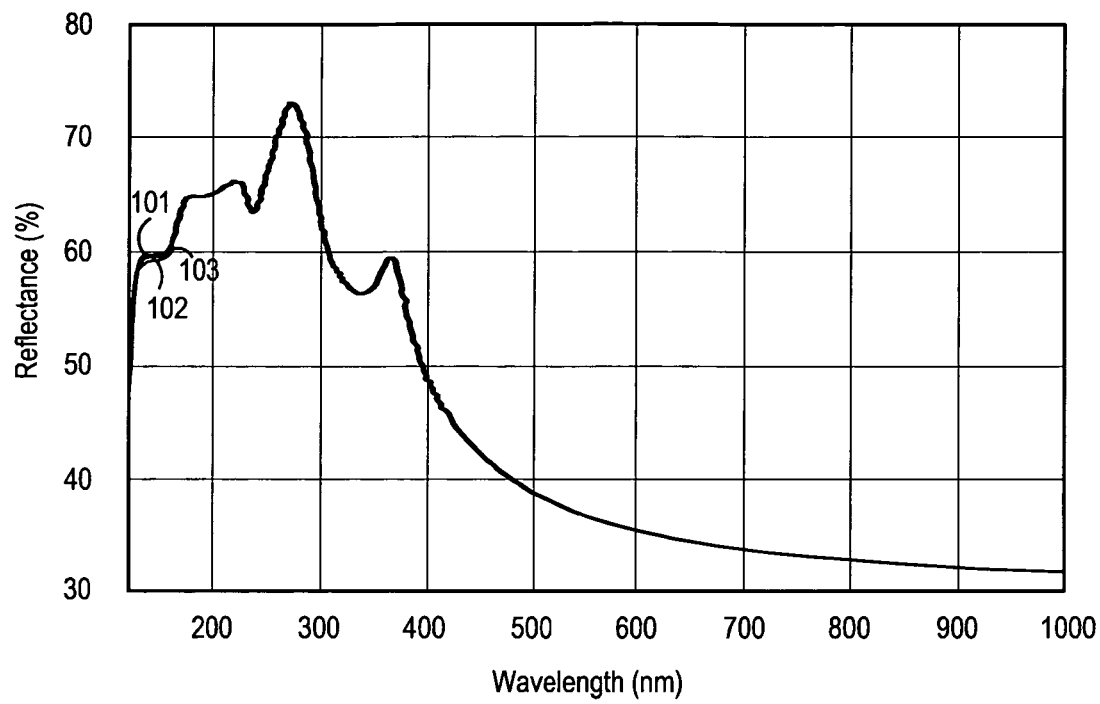
FIGS. 1A and 1B illustrate the effect of changing oxide thickness on reflectance for an ultra thin $SiO_2$ film on silicon substrate.
Figure 1B:
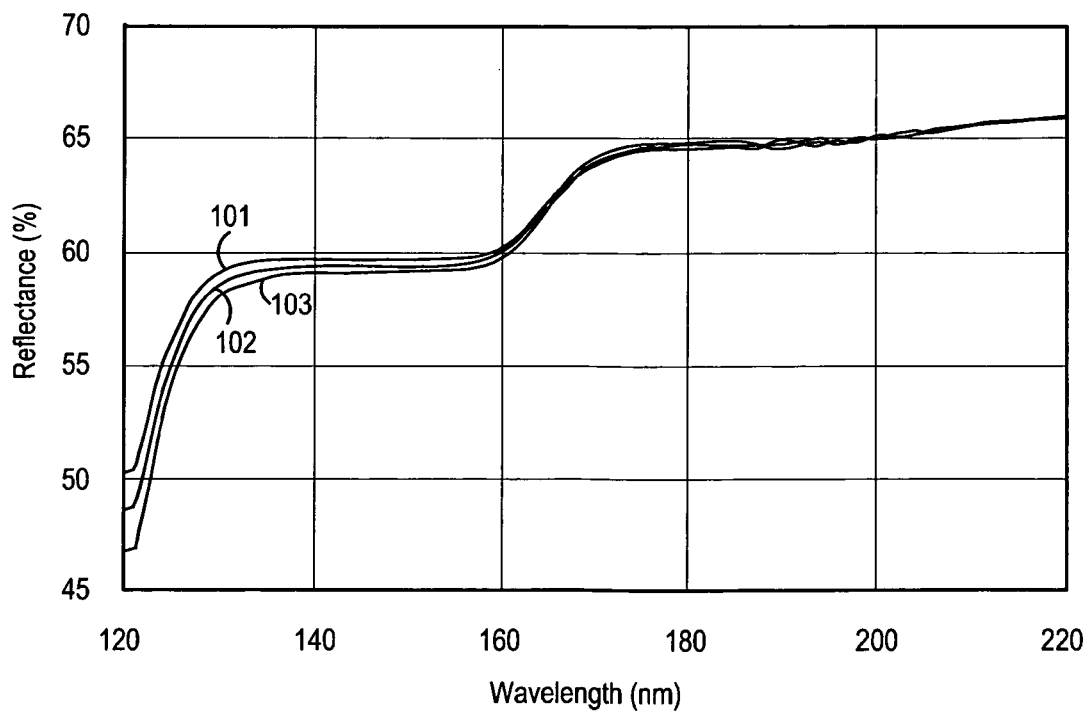
Figure 2A:
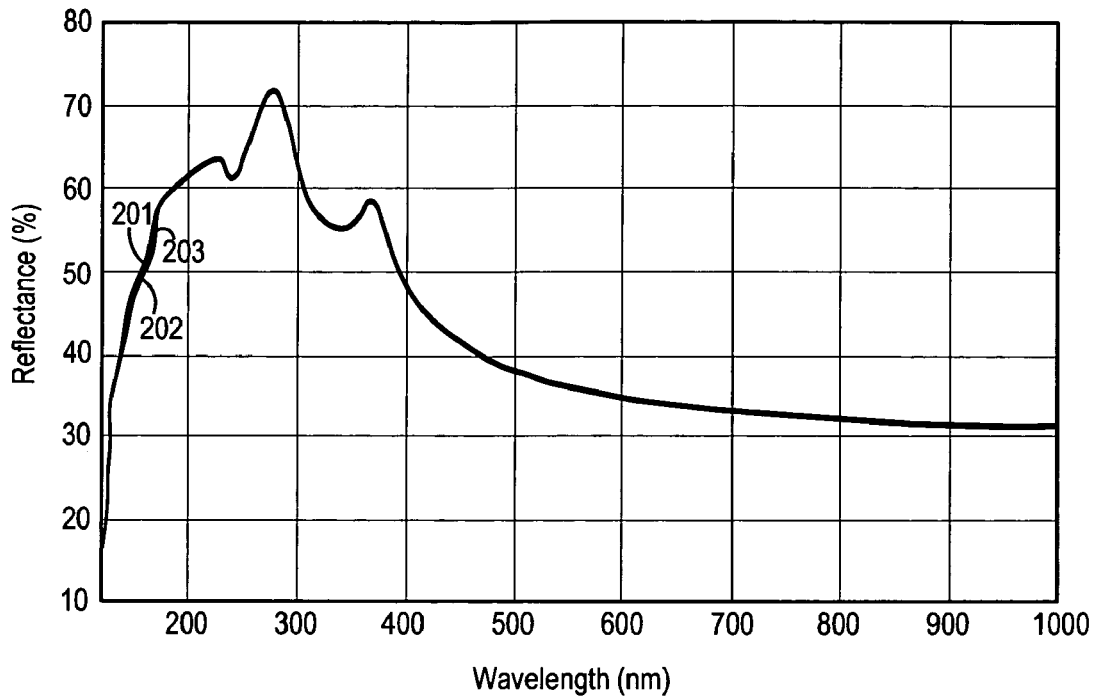
FIGS. 2A-2D illustrate the effect of changing SiON thickness and percent nitride component on reflectance, as well as optical spectra for the oxide and nitride components of an ultra thin SiON film on silicon substrate.
Figure 2B:
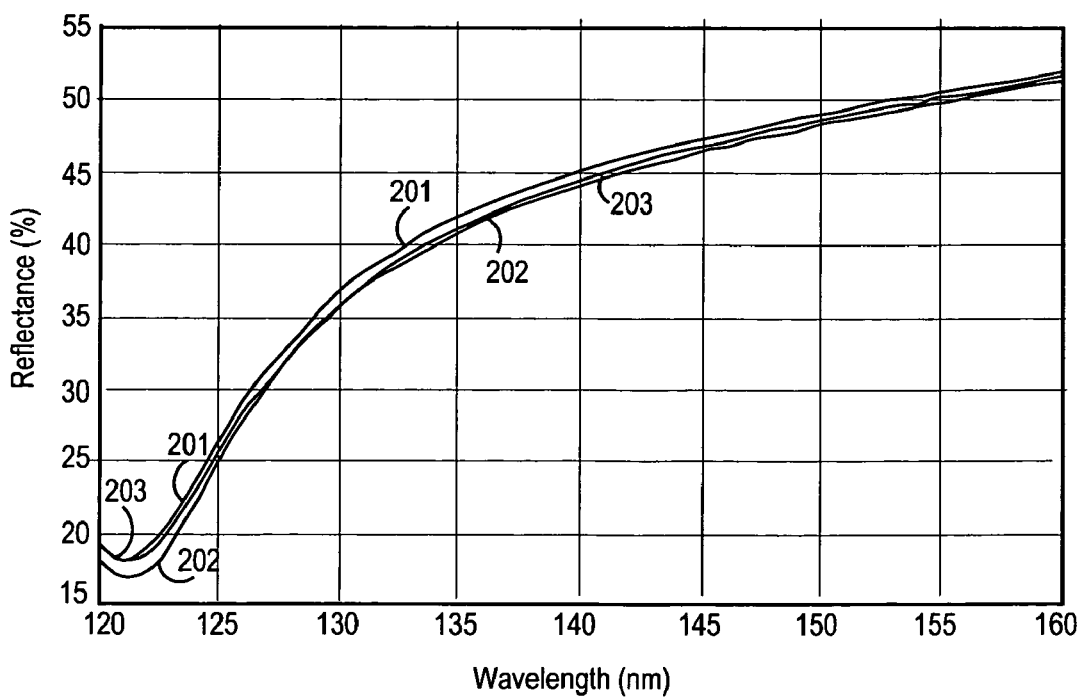
Figure 2C:
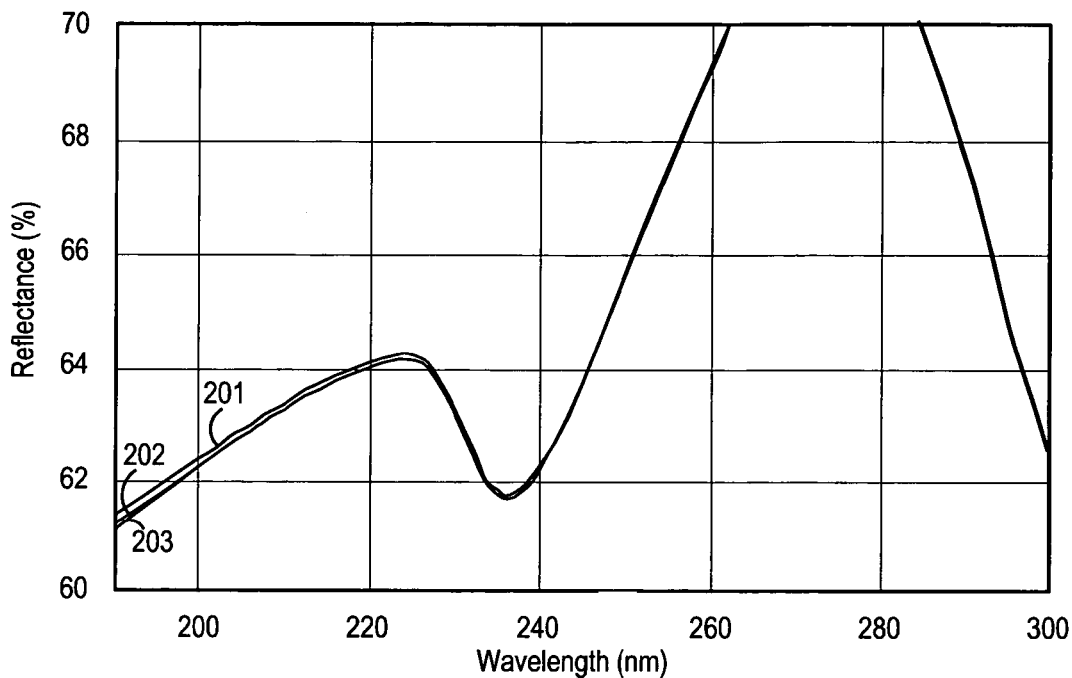
Figure 2D:
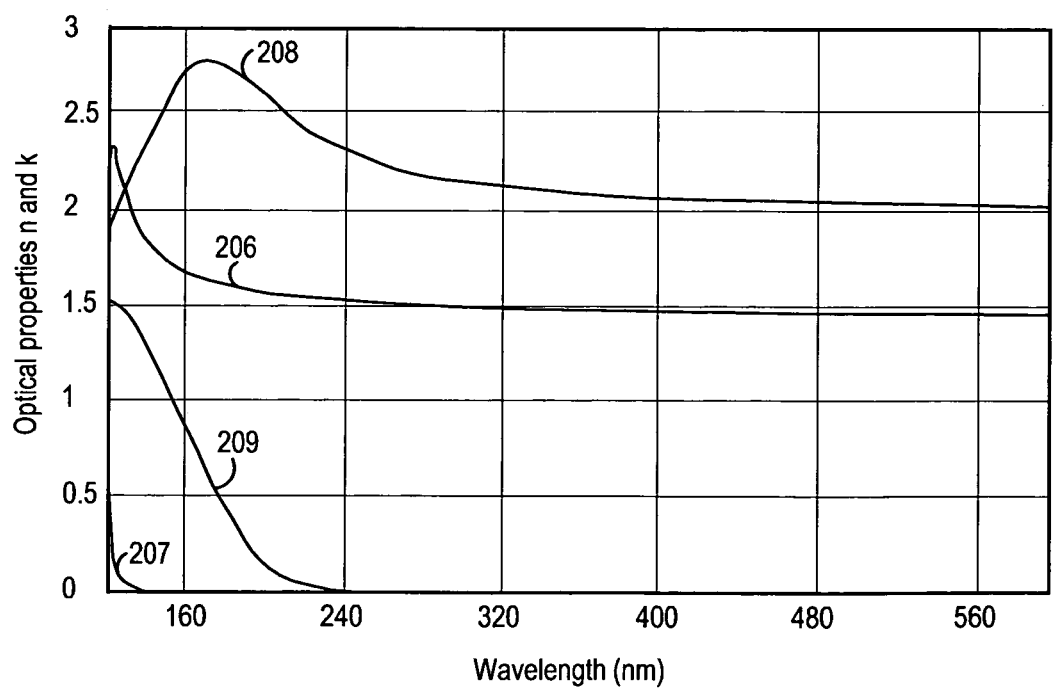

The techniques described herein provide a method and apparatus for reflectometry for measuring properties of thin films or scattering structures on semiconductor work-pieces. In one embodiment vacuum ultraviolet (VUV) wavelength (or lower) reflectometry may be utilized.

Reflectance or ellipsometric data from ultra-thin gate dielectrics are often modeled using an effective medium approximation (EMA), as shown in "The accurate determination of optical properties by ellipsometry", (D. Aspnes, *Handbook of Optical Constants of Solids Volume I*, ed. D. Palik, Academic Press, San Diego, published 1998) that combines two or more constituent components using a single volumetric fraction parameter. Such an approximation is strictly valid when the film dimensions are much smaller than the incident wavelength. Additionally, most EMA approximations make further assumptions about the geometric arrangements of the component materials. For example, the Bruggeman EMA model assumes that the material is a composite mixture of distinct regions, with each region having its own well-defined set of optical properties.

Even if this assumption is not strictly met, for ultra-thin silicon oxynitrides or hafnium silicates, treatment with the Bruggeman EMA model adequately describes the reflectance or ellipsometric data. Additionally, the volume fraction correlates well with the dominant changes in composition, such as percent nitrogen in a silicon oxynitride film. Consequently, for the purposes of this disclosure silicon oxynitride films will be treated as a Bruggeman EMA mixture of $SiO_x$ and $Si_xN_y$ components, while hafnium silicate films are modeled as Bruggeman EMA mixtures of $HfO_x$ and $SiO_x$ components. It is understood that any suitable model could be used in place of the EMA model, and that many film systems could be similarly treated, not limited to silicon oxynitrides and hafnium silicates. Additionally, the methods discussed herein are not limited to just thin film structures, but can also include scattering structures. In particular, the unknown sample could include 1-D or 2-D grating structures, which could be modeled using rigorous diffraction algorithms such as the rigorous coupled wave method.

So described, a model of a silicon oxynitride film consists of the film thickness and EMA mixing fraction of oxide ($SiO_x$) and nitride ($Si_xN_y$) components. The oxide and nitride components themselves are described by their optical properties, index of refraction n and extinction coefficient k, as functions of wavelength. Given the film's thickness and EMA fraction, the reflectance can be calculated at any wavelength using standard thin film Fresnel equations, as described in "Spectroscopic Ellipsometry and Reflectometry—A User's Guide", (H. Tompkins and W. McGahan, John Wiley & Sons Press, New York, published 1999). A metrology measurement is usually performed on an unknown sample by measuring the reflectance of the sample and performing, for example, a Levenberg-Marquardt optimization, as shown in "Numerical Recipes in C ($2^{nd}$ Edition)", (W. H. Press, S. A. Teukolsky, W. T. Vetterling, and B. P. Flanery, Cambridge University Press, Cambridge 1992), with the film thickness and EMA fraction treated as optimization parameters.

A production reflectometer typically does not directly measure the incident intensity (as provided from the source or the actual incident intensity on the measured sample), which is required to measure reflectance of an unknown sample, but instead will determine the incident intensity from the reflected intensity of a known calibration sample. The incident intensity can change over time due to variations in source intensity, environment (temperature and humidity), drift in optical alignment, and the like. A known calibration sample, often a silicon wafer with its native oxide, is first measured, and its reflectance assumed to be known. The incident intensity is determined by dividing the intensity reflected from the calibration sample by its assumed reflectance. The reflectance for an unknown sample is then determined by measuring the intensity reflected from the sample and dividing by the incident intensity.

Obviously, such a calibration method depends on the stability of the calibration sample. In VUV regions, stability is not guaranteed, since small differences in native oxide thicknesses are magnified in that region. In addition, the previously mentioned contamination that occurs confounds the stability of the calibration sample, since the photodeposition occurs every time the calibration sample is measured.

One way to deal with this problem has already been discussed with reference to the calibration techniques disclosed in the U.S. patent applications disclosed above. A measurement of reflectance for a thick (~1000 Å) silicon dioxide on silicon substrate sample relative to a thin oxide sample (typically native silicon dioxide on silicon substrate) is independent of incident intensity, and can be used along with a regression technique to determine both the native oxide thickness as well as contaminant thickness on the thin oxide sample. The result of this analysis is used to calculate the reflectance of the native oxide calibration sample, $R_c$, which is used in combination with the intensity reflected from the calibration sample, $I_c$, to determine the incident intensity via $I_0 = I_c/R_c$. The reflectance of an unknown sample, $R_s$, can then be determined from its reflected intensity, $I_s$, by $R_s = I_s/I_0$.

Disclosed herein is an alternate method for measuring thin film properties that uses reflectance ratios to bypass the system calibration completely. As used herein, the term "calibration" refers to the determination of incident intensity, $I_0$. The method disclosed herein can lead to better long-term performance for some thin film systems, one example being thickness and concentration in ultra-thin silicon oxynitride.

One embodiment of the technique involves measuring the reflected intensity of three samples:

Sample 1—native oxide/Si reference piece,

Sample 2—~1000 Å SiO$_2$/Si reference piece,

Sample 3—the unknown sample (for example an oxynitride sample).

Figure 3:
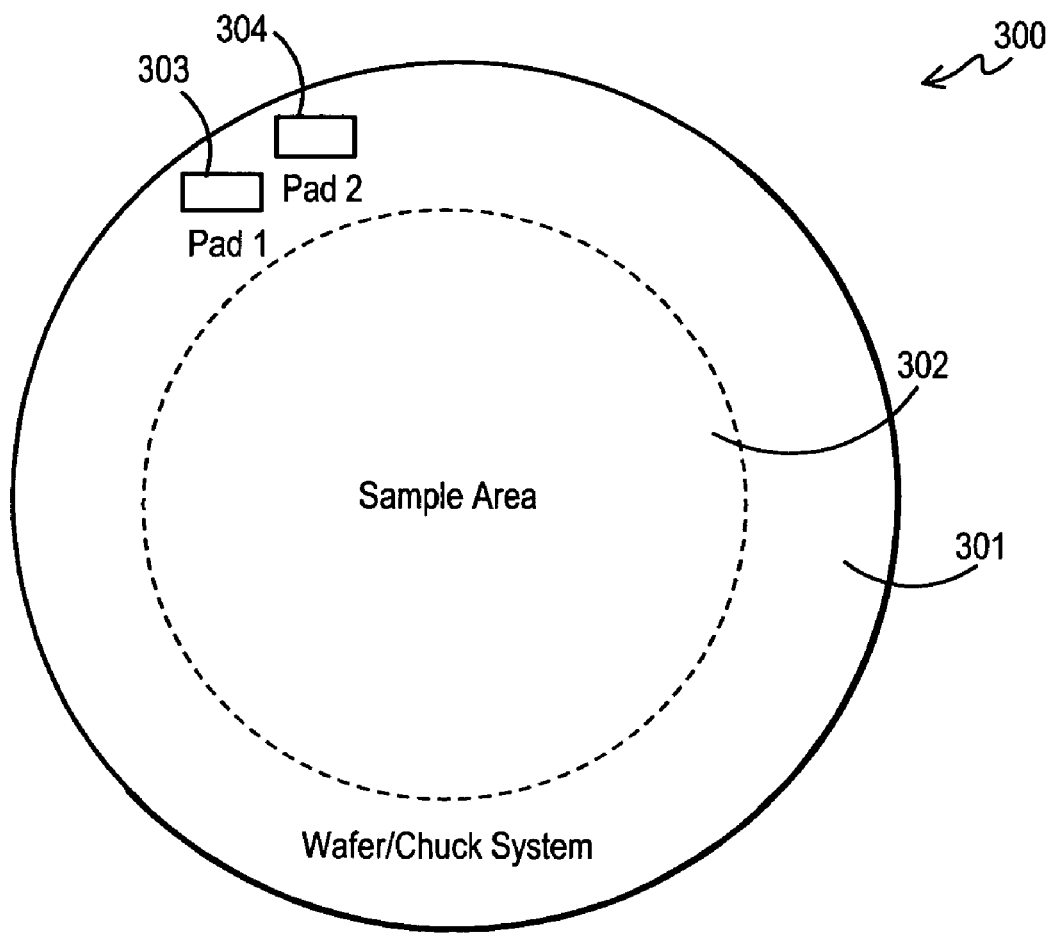
FIG. 3 illustrates a practical embodiment of the current invention, including a movable stage with sample holder and two reference pieces.

The unknown sample will normally consist of a standard silicon substrate of 150 mm, 200 mm, 300 mm, or 450 mm diameter with a deposited film stack. As shown in FIG. 3, the VUV reflectometer discussed in the prior art (U.S. Pat. Nos. 7,026,626, 7,067,818, 7,126,131, and 7,271,394, which are expressly incorporated herein by reference in their entirety) is equipped with a stage and loading port for accepting and measuring reflected intensity at various locations on such a sample which may be placed in sample area 302. The two reference pieces may be small pads, such as pad 1 303 and pad 2 304, mounted on the stage, or at some other location convenient for the wafer/chuck system 301. This reduces the measurement of the reference pieces to basically moving to their locations and collecting intensity data, with no additional wafer handling. FIG. 3 shows an illustration of this arrangement 300. As shown in FIG. 3, the reference pieces are provided integrally with the stage or wafer/chuck system 301 or other sample holder or the like. It will be recognized that the concepts described herein may be utilized with any reference samples and such reference samples do not have to be integrally provided with the stage or wafer/chuck system 301. Thus, as described herein reference pieces such as pads 303 and 304 may be referred to, however, it will be recognized that any reference sample may be provided having the characteristics of the reference pieces.

The unknown sample is loaded into the system 301, and reflected intensities, I1, I2, and I3, are measured for Sample 1, Sample 2, and Sample 3 (for example Sample 1 being pad 1 303 and Sample 2 being Pad 2 304), respectively. Two ratios are formed:

$$I2/I1 = R2/R1, \text{ and}$$

$$I2/I3 = R2/R3. \qquad \text{Eq. 1}$$

The equalities are true as long as $I_0$ has not changed significantly during the measurement of the reflected intensities. $I_0$ is usually stable for at least several minutes, meaning that several locations on Sample 3 could be measured and use the same I1 and I2 in the ratios. I1 and I2 need only be measured with whatever frequency a standard system calibration would normally be performed. An additional embodiment might incorporate the current method and the calibration methods disclosed in U.S. patent application Ser. Nos. 10/930,339, 11/418,827, 11/418,846, and 11/789,686 simultaneously, which are expressly incorporated herein by reference in their entirety. The same pads 303, 304 can be used for calibration of $I_0$ or used as described in the current disclosure, depending on the particular measurement being done. Other ratio combinations can obviously be used as well. As described in more detail herein, the techniques provided herein are particularly advantageous in that the reference pieces need not be stable under the conditions that the reflectometer operates. Thus, reference pieces that, for example, are not stable in the VUV regime may still be utilized. For example, even though the contaminate build-up which may affect a VUV measurement may occur on the reference piece, rendering the reference piece unstable in VUV conditions, the reference piece is still suitable for the techniques described herein.

Thus, during operation instability of the reference sample may relate to the surface of the reference sample changing over time, such as for example, but not limited to contaminant buildup, airborne molecular contaminant removal, growth of films, other time dependent changes, etc. In addition, instability of the reference sample may also relate to inherent non-uniformities of the reference sample (across a given sample or from sample to sample), that may result, for example, from the sample production techniques. For example, bare thicknesses, native oxides, interface properties, surface roughness conditions, etc. may all initially vary across a sample and from sample to sample. Thus these may not change over time, however, from sample to sample or across a sample these conditions may be considered unstable. Thus, as used herein, instability may refer to both time dependent and non-time dependent variations.

The reason for framing the problem in terms of reflectance ratios instead of intensity ratios is that reflectance can be calculated in a straight-forward manner using standard thin film algorithms, as described in "Spectroscopic Ellipsometry and Reflectometry—A User's Guide", (H. Tompkins and W. McGahan, John Wiley & Sons Press, New York, published 1999), along with values for the optical properties and thicknesses of the various films. For instance, if the SiO$_2$ and Si optical properties are known and SiO$_2$ thicknesses provided, the reflectances R1 and R2 can be calculated. Going further, if a measured R2/R1 is available, standard regression techniques can be used to optimize the thicknesses for the SiO$_2$ layers, giving a measurement for both thicknesses, as long as the parameters are sufficiently decoupled. In principle, the optical properties of the SiO$_2$ and Si layers could be determined as well, normally using parameterized dispersion models such as the Tauc-Lorentz model, as shown in "Parameterization of the optical functions of amorphous materials in the interband region", (G. E. Jellison and F. A. Modine, Appl. Phys. Lett., Vol. 69 (1996), p. 371).

In one embodiment, the techniques disclosed herein may be utilized in combination with the techniques disclosed in U.S. patent application Ser. Nos. 10/930,339, 11/418,827, 11/418,846, and 11/789,686. For example, a measurement software routine may be selectable between differing modes, a first mode being the techniques described herein and a second mode being the techniques described in the above mentioned U.S. patent applications. Thus, the system may selectably operate (automatically or based on user input) in at least one of a plurality of measurement modes, the plurality of measurement modes including at least a first measurement mode and a second measurement mode. The first measurement mode may be configured to utilize a combination of the unknown sample and reference sample data that is independent of incident intensity to determine a property of the unknown sample, without calibrating incident reflectometer intensity as described herein in more detail. The second measurement mode may be configured to utilize the reference sample data in a manner that is independent of incident intensity to determine one or more properties of one or more reference pieces, thereby determining the incident intensity of the reflectometer, after which reflectance of unknown samples may be determined such as described in the above referenced U.S. patent application Ser. Nos. 10/930,339, 11/418,827, 11/418,846, and 11/789,686.

The current method disclosed herein involves a regression analysis of both ratios in Equation 1 simultaneously. Basically, the parameters in the modeled ratios are optimized until both calculated ratios R2/R1 and R2/R3 agree with their corresponding measured ratios. One way to do the optimization is to use a version of the Levenberg-Marquardt routine generalized to multiple sample analysis. In such cases, the nonlinear chi-square merit function could be written as:

$$\chi^2 = \sum_{i=1}^{N21} \left(\frac{1}{\sigma_i}\right)^2 \left(\left(\frac{R2}{R1}\right)_{i,measured} - \left(\frac{R2}{R1}\right)_{i,calculated}\right)^2 + \qquad \text{Eq. 2}$$

$$\sum_{j=1}^{N23} \left(\frac{1}{\sigma_j}\right)^2 \left(\left(\frac{R2}{R3}\right)_{j,measured} - \left(\frac{R2}{R3}\right)_{j,calculated}\right)^2$$

where the $\sigma_i$ and $\sigma_j$ are estimates of the standard error for each measured data point. The notation on the summation limits, N21 and N23, illustrates that the data range for the two datasets does not have to be the same.

The results of the optimization procedure are the measured parameters for all three samples. The reference pads 303, 304 will ordinarily undergo contaminant buildup due to extended use in the system, and so a contaminant layer will be included in the reflectance models for the reference pieces. Thus the result of the analysis include the thicknesses of both oxide (native and ~1000 Å) thicknesses, thickness of contaminant in both reference pieces, and all of the same regression parameters for the unknown sample that would have been varied during a standard optical measurement, such as film thicknesses and optical properties (via the EMA fraction in the ultra-thin SiON case). The redundancy provided by having sample 2 involved in both datasets helps constrain the problem and yield better results for the unknown sample.

A series of simulations will follow to illustrate the usefulness of the method in the case of ultra-thin silicon oxynitride (SiON) gate films, which serve the role of Sample 3. For the purposes of this description, the optical properties n and k of the silicon native oxide, silicon dioxide ($SiO_2$), silicon (Si), Silicon Nitride ($Si_3N_4$), and contaminant are regarded as known. The optical values were taken from a variety of literature sources or determined through other measurements. In particular, the contaminant optical properties could be determined using a controlled experiment similar to the methods disclosed in U.S. patent application Ser. No. 11/789,686, which is expressly incorporated herein by reference in its entirety. The SiON films are treated as Bruggeman EMA films composed of $SiO_2$ and $Si_3N_4$. Aside from the optical properties, a full description of the ultra-thin oxynitride film is considered to be a specification of its thickness and EMA volume fraction. The volume fraction can be correlated to nitrogen content in the films, which is an important process control parameter along with the film thickness. In the present example, treatment of explicit interface layers and surface and interface roughness are ignored, but such effects could also be included in the models, if desired.

Figure 4A:
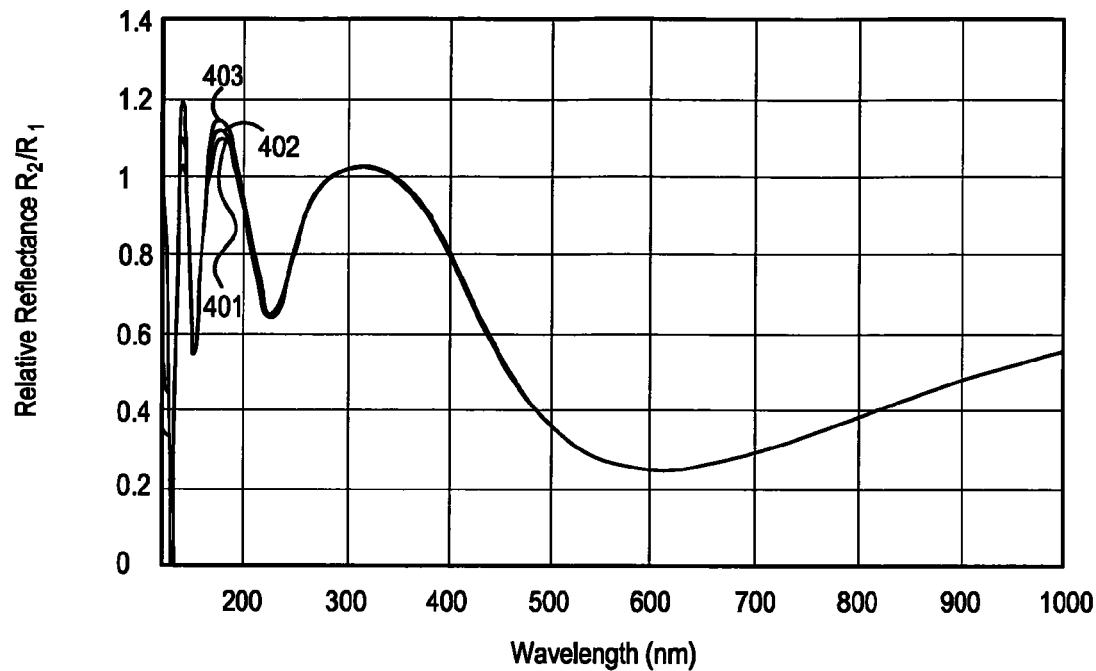
FIGS. 4A and 4B illustrate variation in a reflectance ratio due to changing native oxide thickness.
Figure 4B:
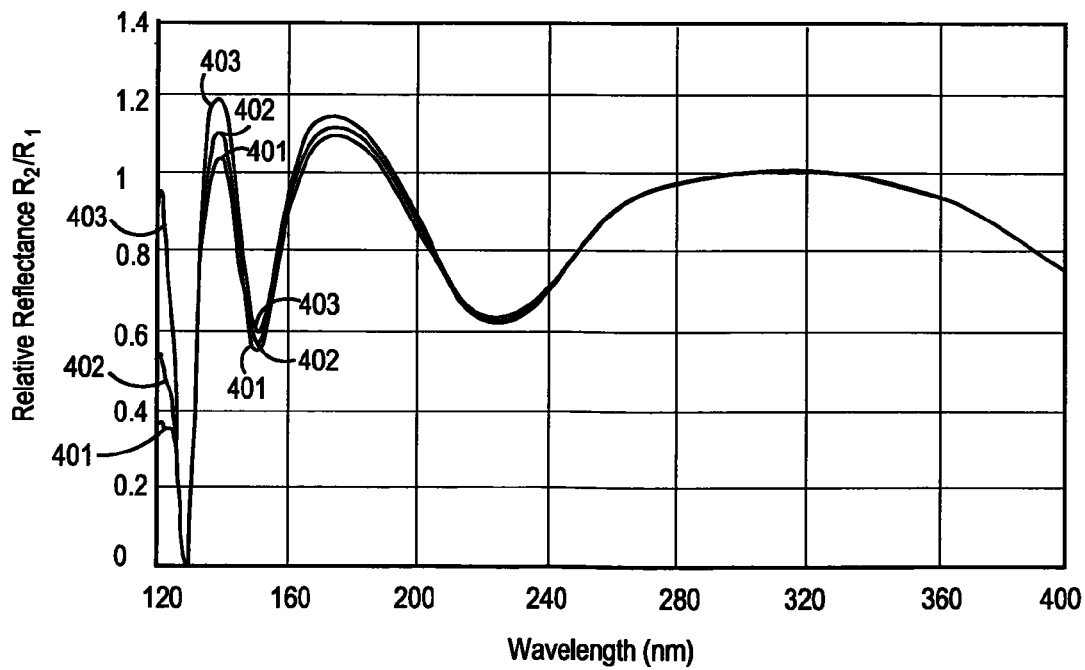
Figure 5A:
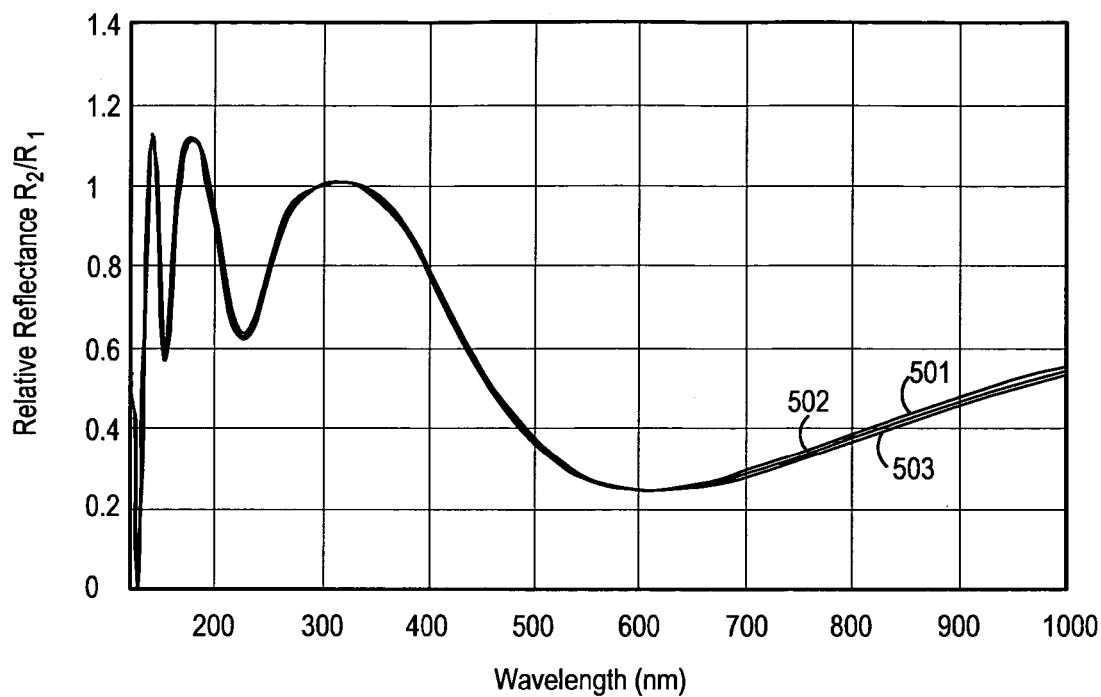
FIGS. 5A and 5B illustrate variation in a reflectance ratio due to changing ~1000 Å $SiO_2$ thickness.
Figure 5B:
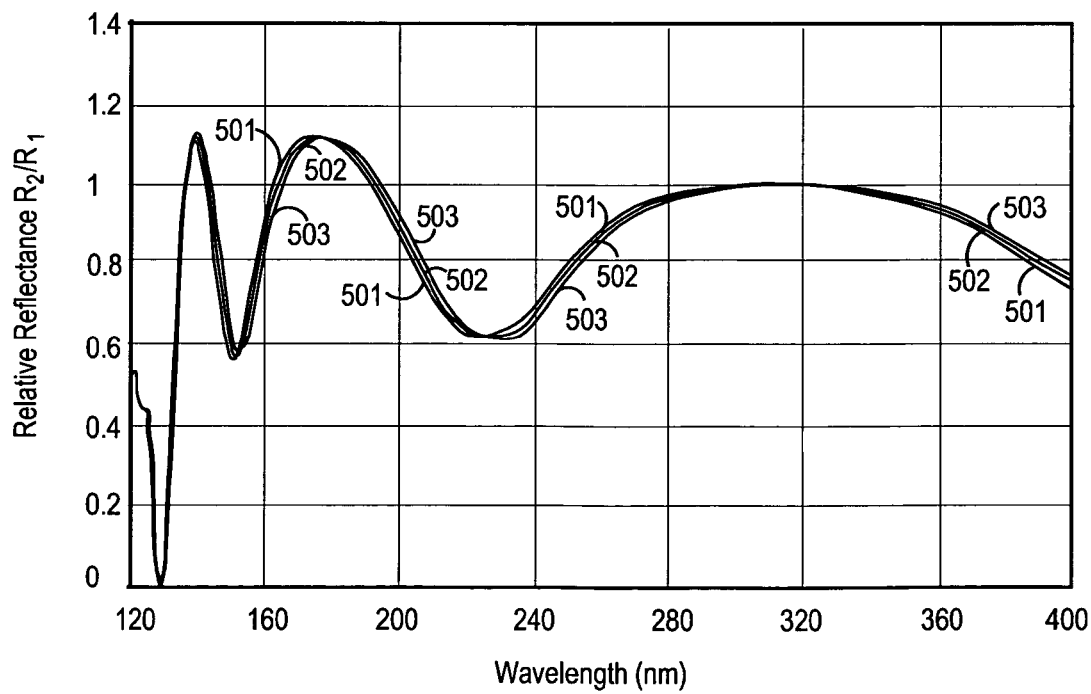

FIGS. 4A and 4B show simulations of the variation of the ratio R2/R1, where R2 is the simulated reflectance of a 1000 Å $SiO_2$ on Si substrate and R1 is the simulated reflectance of 10 Å $SiO_2$ (plot 401), 20 Å $SiO_2$ (plot 402), and 30 Å $SiO_2$ (plot 403) on Si substrate samples. FIG. 4A shows a relative reflectance range of 0 to 1.4, and a wavelength range of 120 nm to 1000 nm. FIG. 4B is an expanded version of a portion of FIG. 4A, and shows a relative reflectance range of 0 to 1.4, and a wavelength range of 120 nm to 400 nm. FIGS. 5A and 5B show similar ratios with R1 fixed at 20 Å $SiO_2$ on Si substrate and R2 varied from 1000 Å $SiO_2$ (plot 501), 1010 Å $SiO_2$ (plot 502), and 1020 Å $SiO_2$ (plot 503) on Si substrate. FIG. 5A shows a relative reflectance range of 0 to 1.4, and a wavelength range of 120 nm to 1000 nm. FIG. 5B is an expanded version of a portion of FIG. 5A, and shows a relative reflectance range of 0 to 1.4, and a wavelength range of 120 nm to 400 nm. Clearly, the effects of changing thickness of the thin and thick oxides in these ratios are decoupled, and may be readily extracted from measured ratios through regression procedures. The measured ratio is simply the ratio of the reflected intensities of the two samples, which is independent of $I_0$ if only a short time has passed between the intensity measurements.

Figure 6A:
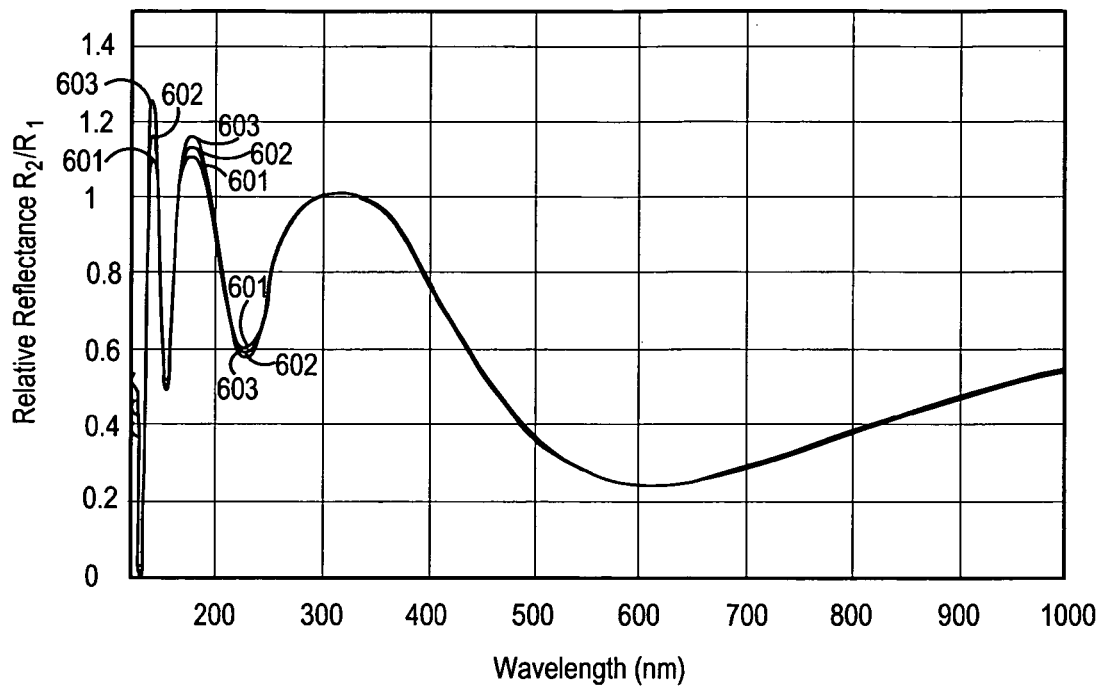
FIGS. 6A and 6B illustrate variation in a reflectance ratio due to changing contaminant thickness on both a ~1000 Å $SiO_2$ on silicon sample and native oxide on silicon sample.
Figure 6B:
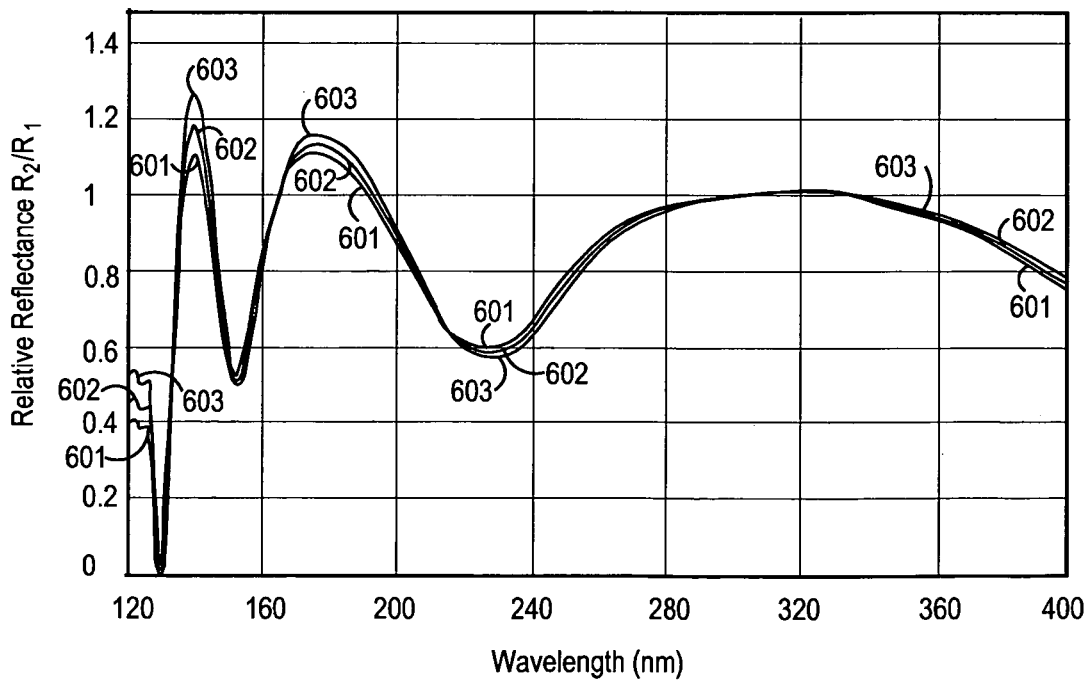
Figure 7A:
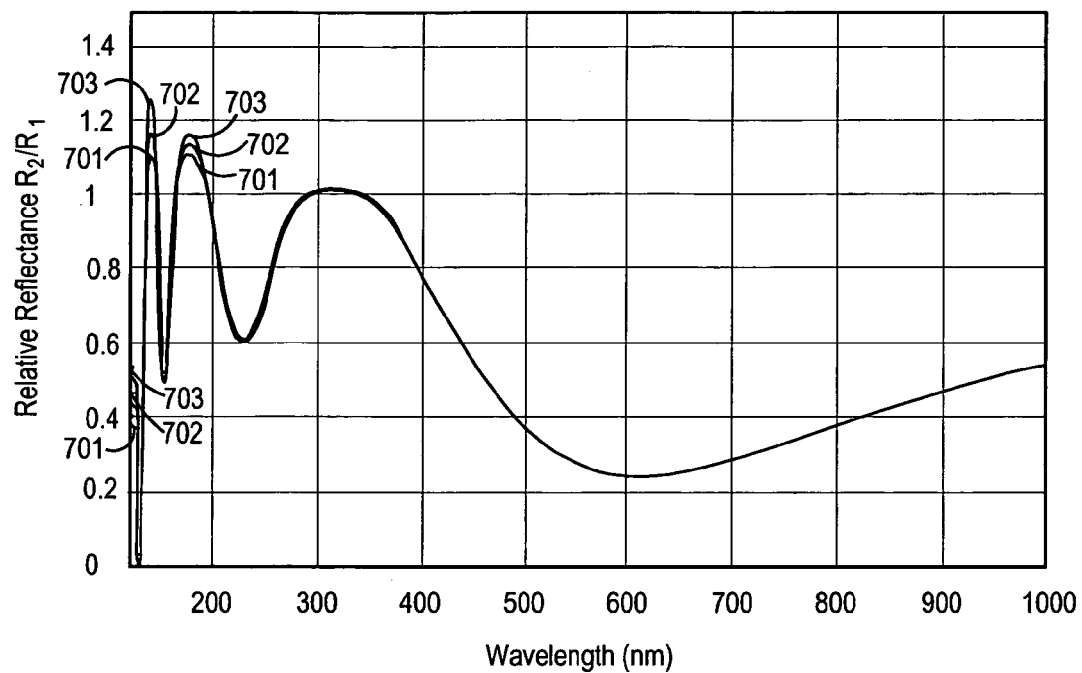
FIGS. 7A and 7B illustrate variation in a reflectance ratio due to changing contaminant thickness on the native oxide sample.
Figure 7B:
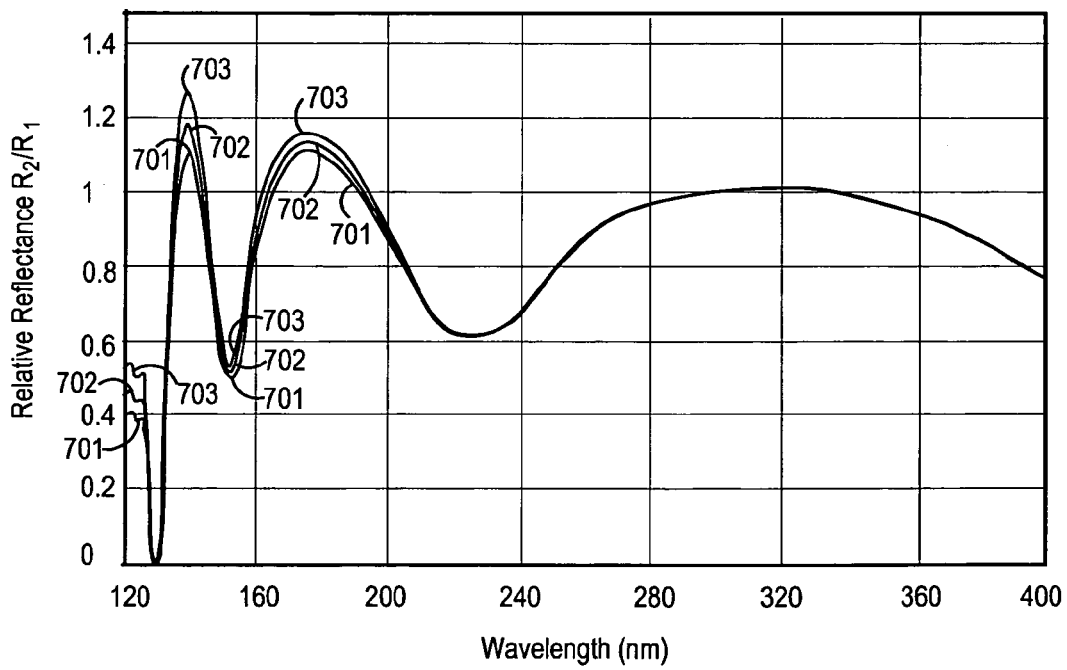
Figure 8A:
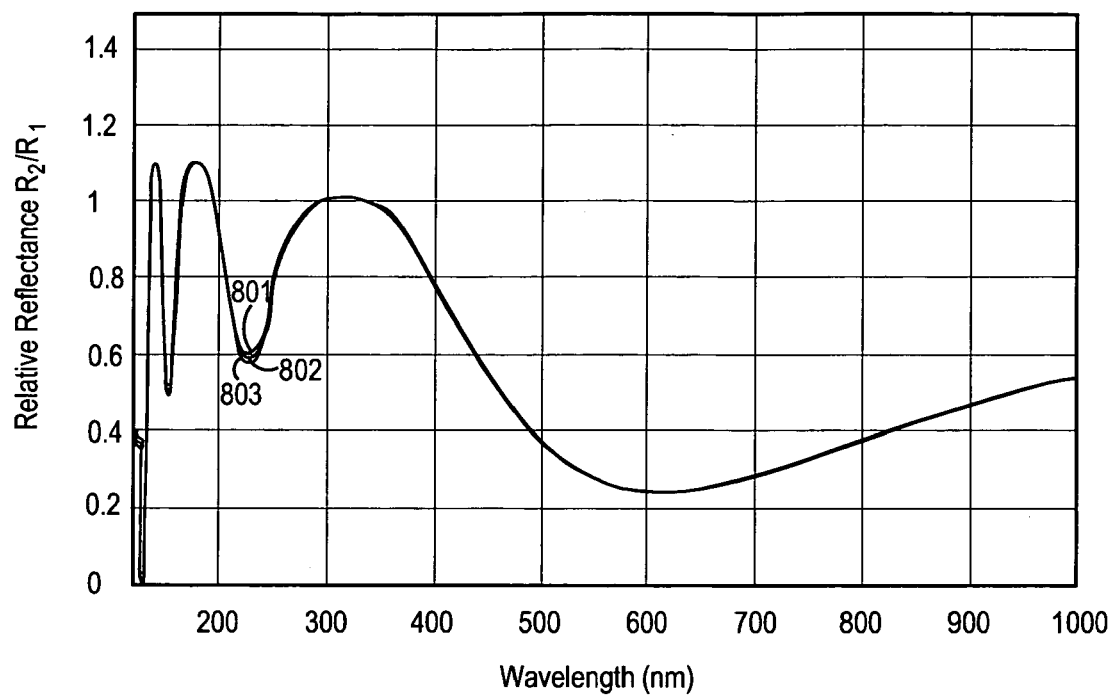
FIGS. 8A and 8B illustrate variation in a reflectance ratio due to changing contaminant thickness on the ~1000 Å $SiO_2$ sample.
Figure 8B:
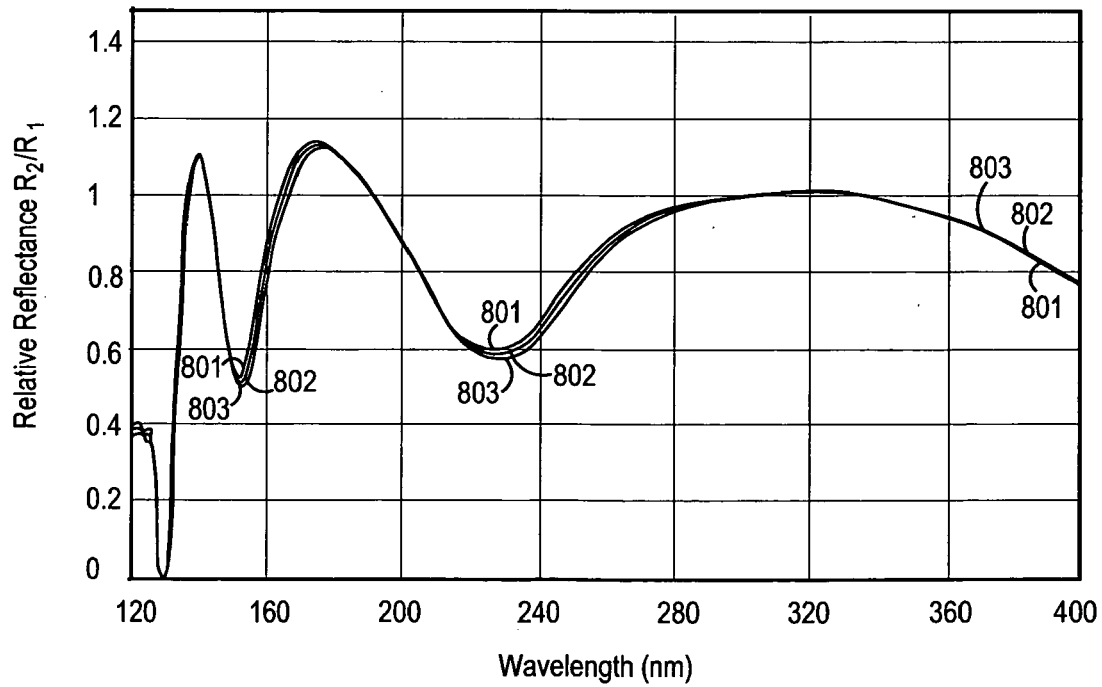

FIGS. 6A, 6B, 7A, 7B, 8A, and 8B show the effects of contaminant buildup on both calibration samples. In FIGS. 6A and 6B, a reflectance ratio of 10 Å contaminant on 1000 Å SiO2 on Si and 10 Å contaminant on 10 Å SiO2 on Si is shown as plot 601, 20 Å contaminant on 1000 Å SiO2 on Si and 20 Å contaminant on 10 Å SiO2 on Si is shown as plot 602, and 30 Å contaminant on 1000 Å SiO2 on Si and 30 Å contaminant on 10 Å SiO2 on Si is shown as plot 603. FIG. 6A shows a relative reflectance range of 0 to 1.4, and a wavelength range of 120 nm to 1000 nm. FIG. 6B is an expanded view of FIG. 6A, and shows a relative reflectance range of 0 to 1.4, and a wavelength range of 120 nm to 400 nm. The optical properties for the contaminant layer were determined from a prior reflectance ratio analysis study. FIGS. 7A and 7B illustrate that the effect of increasing contaminant buildup on the native oxide sample is to primarily increase the ratio in the VUV, as the reflectance of the native oxide sample decreases. In FIGS. 7A and 7B, a reflectance ratio of 10 Å contaminant on 1000 Å SiO2 on S and 10 Å contaminant on 10 Å SiO2 on Si is shown as plot 701, 10 Å contaminant on 1000 Å SiO2 on Si and 20 Å contaminant on 10 Å on SiO2 on Si is shown as plot 702, and 10 Å contaminant on 1000 Å SiO2 on Si and 30 Å contaminant on 10 Å SiO2 on Si is shown as plot 703. FIG. 7A shows a relative reflectance range of 0 to 1.4, and a wavelength range of 120 nm to 1000 nm. FIG. 7B is an expanded version of a portion of FIG. 7A, and shows a relative reflectance range of 0 to 1.4, and a wavelength range of 120 nm to 400 nm. In contrast, the effect of growing contaminant on the 1000 Å $SiO_2$/Si sample, as seen in FIGS. 8A and 8B, is to increase the interference amplitude minima and simultaneously shift the locations of the interference minima to longer wavelengths. In FIGS. 8A and 8B, a reflectance ratio of 10 Å contaminant on 1000 Å SiO2 on Si and 10 Å contaminant on 10 Å SiO2 on Si is shown as plot 801, 20 Å contaminant on 1000 Å SiO2 on Si and 10 Å contaminant on 10 Å SiO2 on Si is shown as plot 802, and 30 Å contaminant on 1000 Å SiO2 on Si and 10 Å contaminant on 10 Å SiO2 on Si is shown as plot 803. FIG. 8A shows a relative reflectance range of 0 to 1.4, and a wavelength range of 120 nm to 1000 nm. FIG. 5B is an expanded version of a portion of FIG. 8A, and shows a relative reflectance range of 0 to 1.4, and a wavelength range of 120 nm to 400 nm.

Comparisons of FIGS. 6A, 6B, 7A, 7B, 8A, and 8B with FIGS. 4A, 4B, 5A, and 5B also show that the contaminant buildup is decoupled from changes in the 1000 Å $SiO_2$/Si thickness. The contaminant is also decoupled from the thin oxide thickness, although the effects on the ratio are more subtle. In practice, the regression procedure is able to extract the correct changes, and this method is effective at accounting for changes in reflectance of the 1000 Å and native oxide calibration samples without knowing the changes a priori.

Figure 9A:
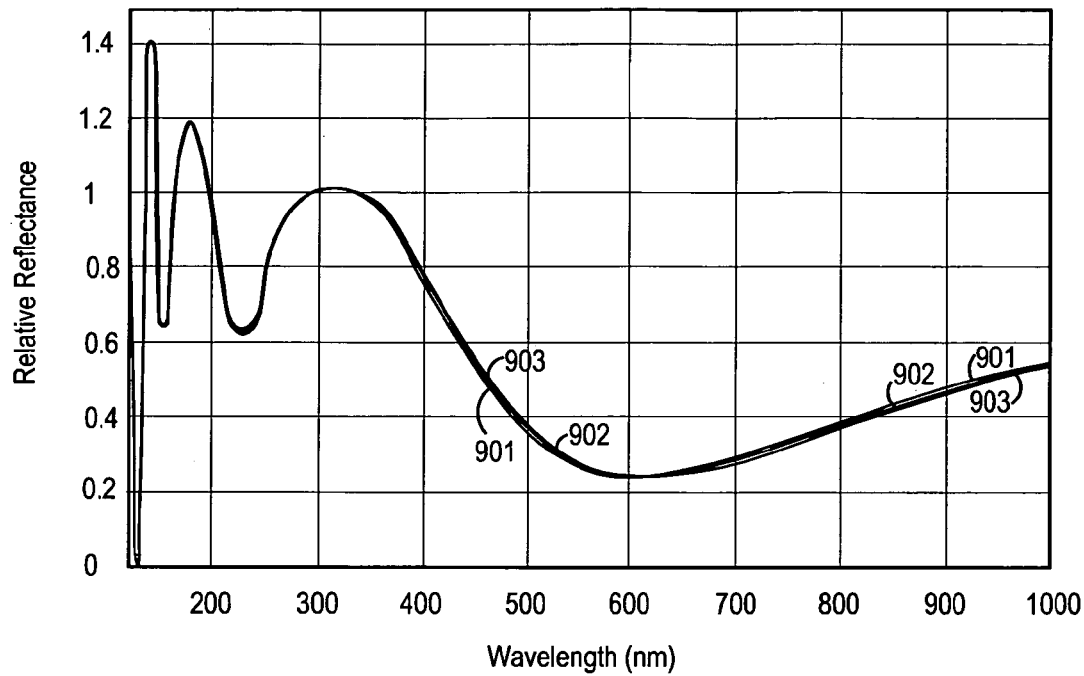
FIGS. 9A and 9B illustrate variation in a reflectance ratio of ~1000 Å $SiO_2$ on silicon and an ultra thin SiON on silicon sample due to changing $SiO_2$ thickness.

FIGS. 9A-12B show simulations of several R2/R3 ratios. FIGS. 9A and 9B show 1000 Å $SiO_2$ (plot 901), 1010 Å $SiO_2$ (plot 902) and 1020 Å $SiO_2$ (plot 903) on silicon (R2) relative to a 30 Å, 15% EMA volume fraction SiON on silicon film as R3, illustrating the effects of changing $SiO_2$ thickness on the R2/R3 ratio. FIG. 9A shows a relative reflectance range of 0 to 1.4, and a wavelength range of 120 nm to 1000 nm. FIG. 9B is an expanded version of a portion of FIG. 9A, and shows a relative reflectance range of 0 to 1.4, and a wavelength range of 120 nm to 400 nm.

Figure 9B:
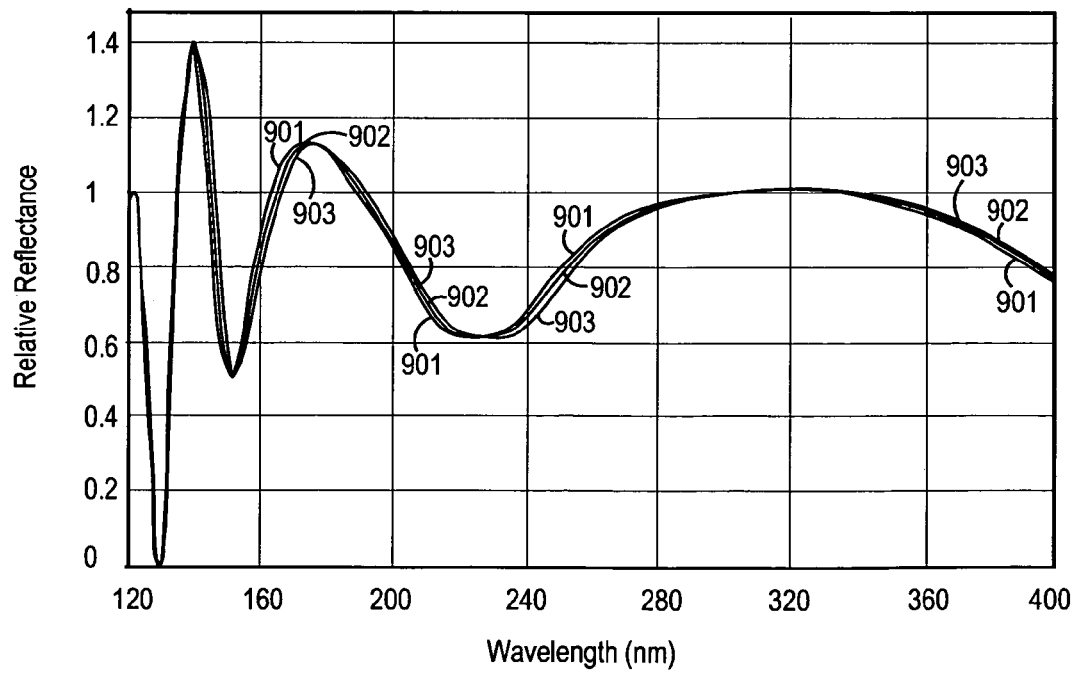
Figure 10A:
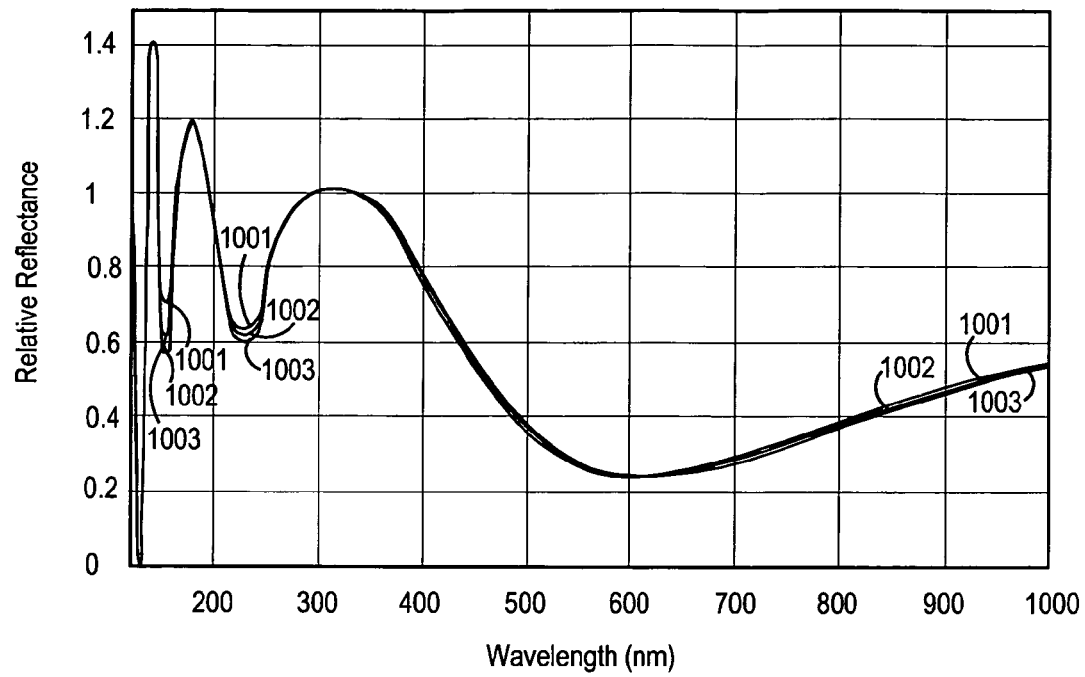
FIGS. 10A and 10B illustrate variation in a reflectance ratio of a ~1000 Å $SiO_2$ on silicon and an ultra thin SiON on silicon sample due to changing contaminant thickness on the ~1000 Å $SiO_2$ sample.
Figure 10B:
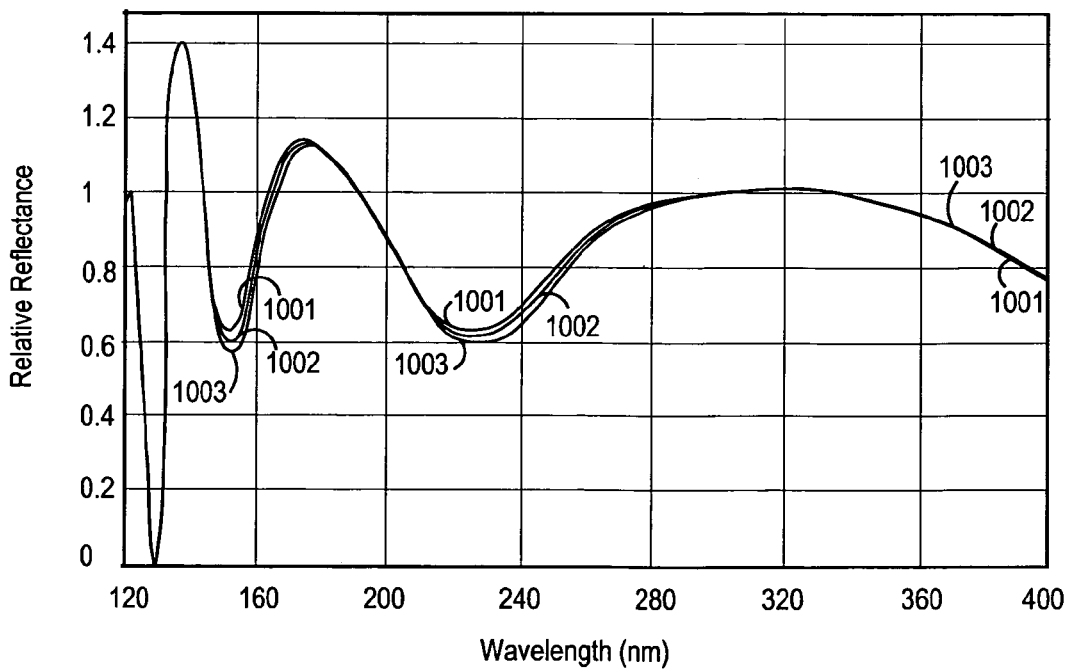

FIGS. 10A and 10B show ratios with 0 Å contaminant buildup (plot 1001), 10 Å contaminant buildup (plot 1002), and 20 Å of a contaminant buildup (plot 1003) on the 1000 Å $SiO_2$ on silicon sample, with R3 the same 30 Å, 15% fraction SiON film as in FIGS. 9A and 9B. FIG. 10A shows a relative reflectance range of 0 to 1.4, and a wavelength range of 120 nm to 1000 nm. FIG. 10B is an expanded version of a portion of FIG. 10A, and shows a relative reflectance range of 0 to 1.4, and a wavelength range of 120 nm to 400 nm.

Figure 11A:
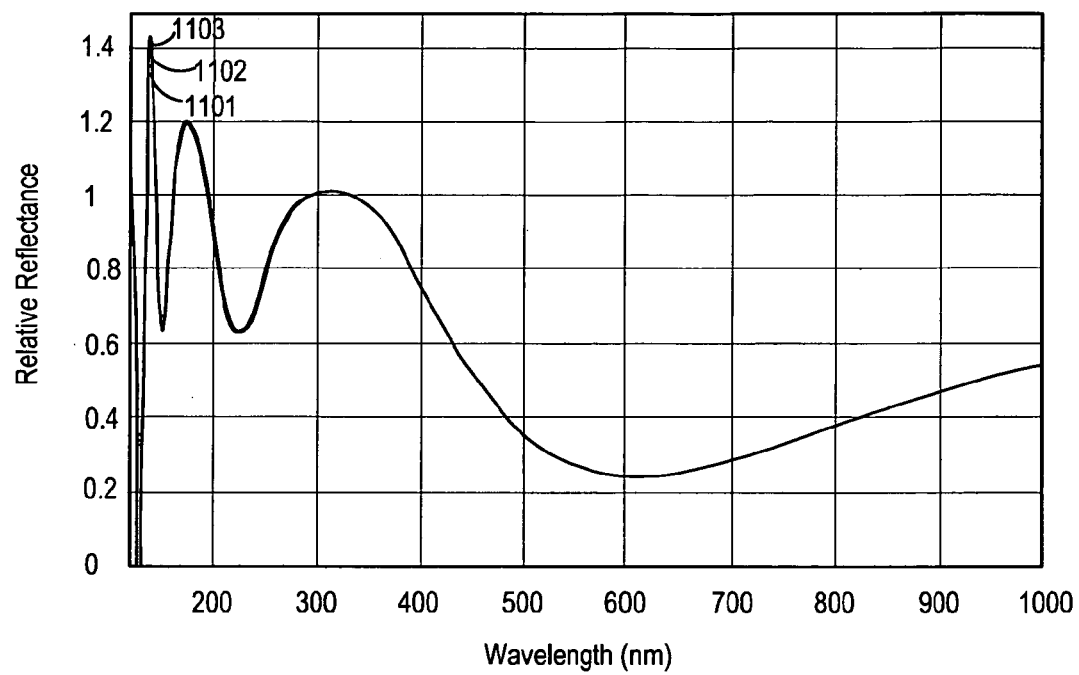
FIGS. 11A and 11B illustrate variation in a reflectance ratio of a ~1000 Å $SiO_2$ on silicon and an ultra thin SiON on silicon sample due to changing SiON thickness.
Figure 11B:
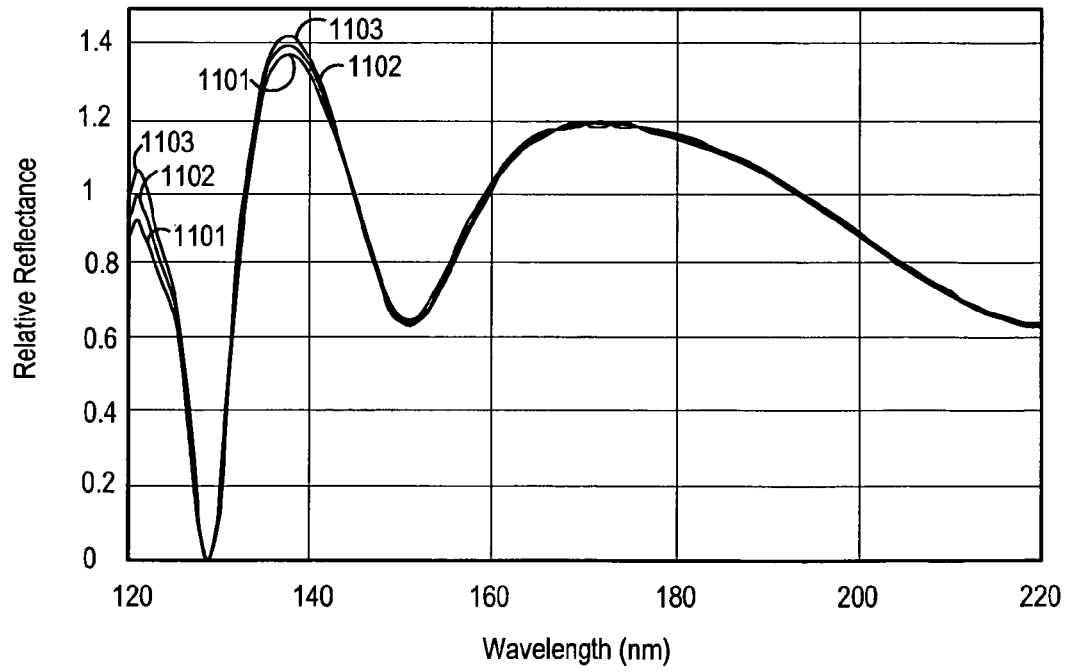
Figure 12A:
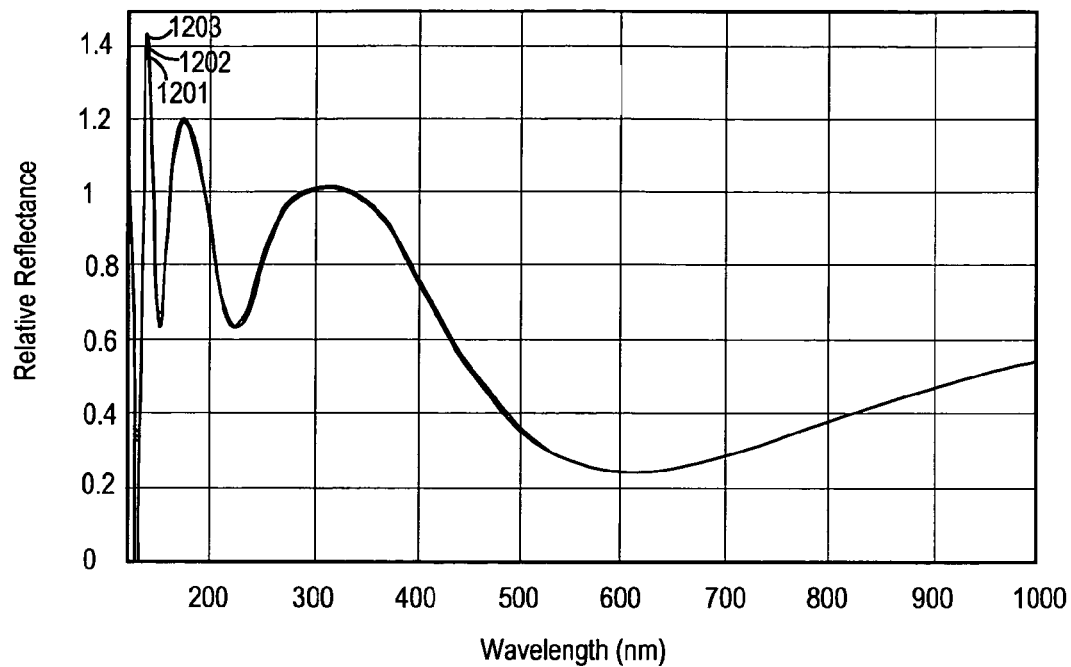
FIGS. 12A and 12B illustrate variation in a reflectance ratio of a ~1000 Å $SiO_2$ on silicon and an ultra thin SiON on silicon sample due to changing SiON percent nitrogen content.
Figure 12B:
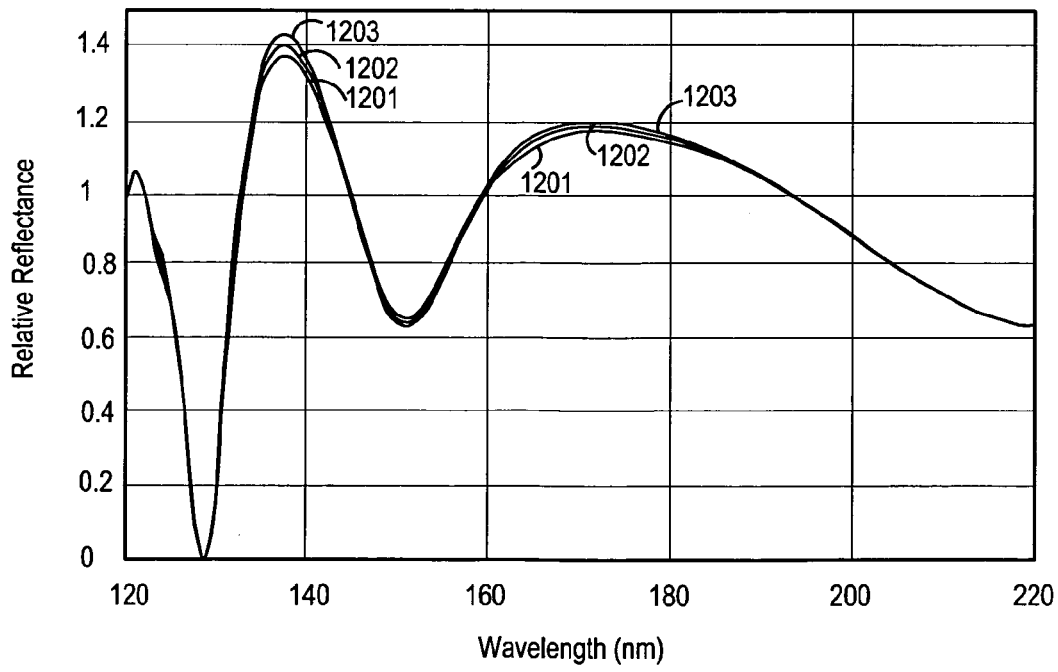

FIGS. 11A and 11B show the effects of changing SiON thickness (29 Å (plot 1101), 30 Å (plot 1102), 31 Å (plot 1103), 15% EMA fraction) on the R2/R3 ratio, and FIGS. 12A and 12B show the effects of changing EMA % (30 Å, 13% (plot 1201), 15% (plot 1202), 17% (plot 1203) EMA fractions) on the ratio. FIG. 11A shows a relative reflectance range of 0 to 1.4, and a wavelength range of 120 nm to 1000 nm. FIG. 11B is an expanded version of a portion of FIG. 11A, and shows a relative reflectance range of 0 to 1.4, and a wavelength range of 120 nm to 220 nm. FIG. 12A shows a relative reflectance range of 0 to 1.4, and a wavelength range of 120 nm to 1000 nm. FIG. 12B is an expanded version of a portion of FIG. 12A, and shows a relative reflectance range of 0 to 1.4, and a wavelength range of 120 nm to 220 nm.

If Sample 2 did not change, the reflectance of Sample 3 could be extracted directly from the ratios in FIGS. 11A, 11B, 12A, and 12B. If one inspects the figures closely, it is apparent that the effect of changing SiON thickness is to decrease the VUV portion of the R3 spectrum (with corresponding increase in R2/R3), and the effect of changing the EMA % is to bend the shape of the R3 spectrum, with anchor points near 120 nm and 220 nm. However, Sample 2 is not stable, but builds up contaminant over time, the effect of which was shown in FIGS. 10A and 10B. An analysis of R2/R3 alone might reasonably be expected to exhibit some coupling, especially between contaminant thickness on the Sample 2 piece and EMA % of the SiON film. Analyzing the R2/R1 ratio simultaneously with the R2/R3 ratio helps to constrain the possible values of R2 contaminant thickness, since the properties of R2 are the same for both ratios. This in turn enhances the determination of the R3 properties.

Figure 13A:
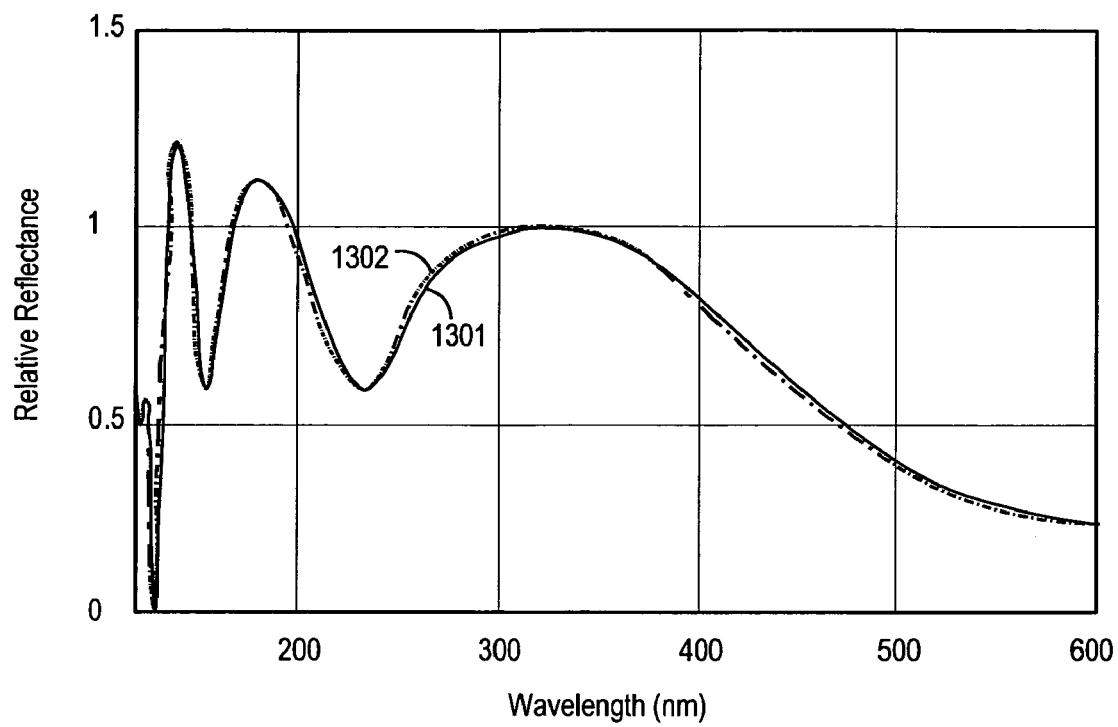
FIGS. 13A and 13B illustrate a measured and fit reflectance ratio of a ~1000 Å $SiO_2$ on silicon and a native oxide on silicon sample.
Figure 13B:
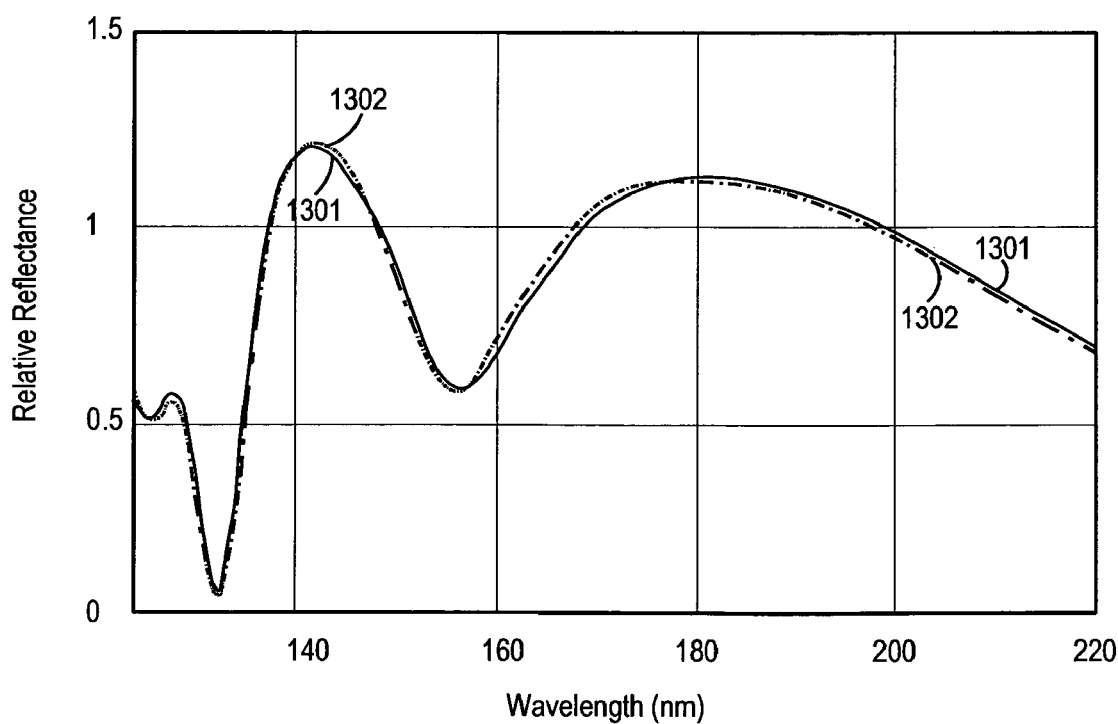
Figure 13C:
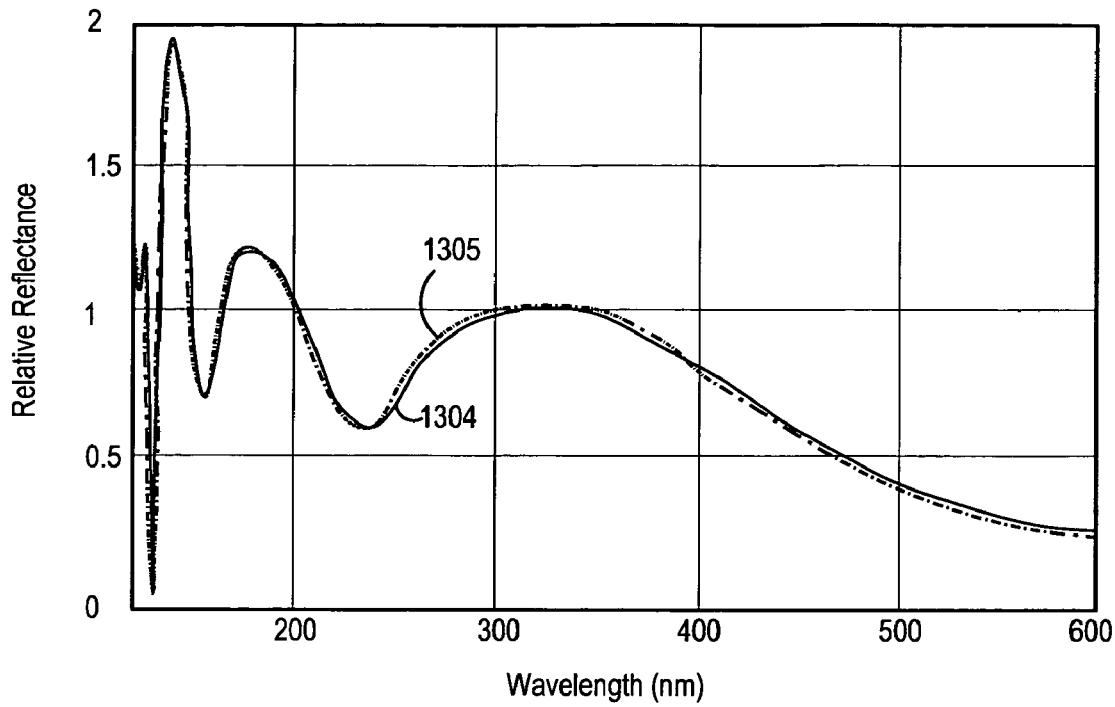
FIGS. 13C and 13D illustrate a measured and fit reflectance ratio of a ~1000 Å $SiO_2$ on silicon and an ultra thin SiON sample.
Figure 13D:
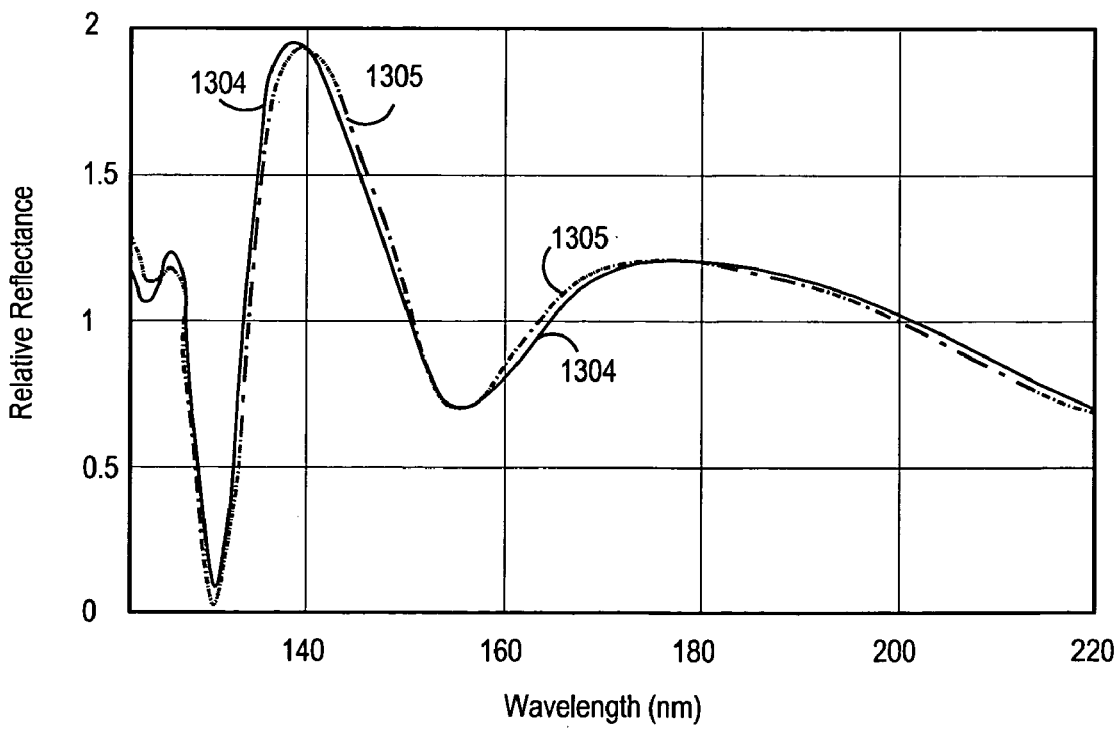

An example of a simultaneous multiple ratio fit of a SiON film is shown in FIGS. 13A-13D. The raw data consists of reflected intensities from two reference pieces consisting of native oxide and ~1000 Å $SiO_2$ films on silicon, and a central location on a SiON sample. As described above, the ratios R2/R1 measured (plot 1301) and modeled (plot 1302) shown in FIGS. 13A and 13B, and R2/R3 measured (plot 1304) and modeled (plot 1305) shown in FIGS. 13C and 13D were simultaneously analyzed, resulting in optimized parameters for all three samples. The results of the optimization shown in FIGS. 13A-13D are 12.041 Å contaminant and 19.242 Å $SiO_2$ for Sample 1, 7.275 Å contaminant and 1045.8 Å $SiO_2$ for Sample 2, and 31.709 Å thickness and 16.036% nitrogen for Sample 3. The fit parameters for R2 were constrained to be the same for both ratios. FIG. 13A shows a relative reflectance range of 0 to 1.5, and a wavelength range of 120 nm to 600 nm. FIG. 13B is an expanded version of a portion of FIG. 13A, and shows a relative reflectance range of 0 to 1.5, and a wavelength range of 120 nm to 220 nm. FIG. 13C shows a relative reflectance range of 0 to 2, and a wavelength range of 120 nm to 600 nm. FIG. 13D is an expanded version of a portion of FIG. 13C, and shows a relative reflectance range of 0 to 2, and a wavelength range of 120 nm to 220 nm.

In some embodiments, the underlying oxide and possibly even interface regions of the reference pieces can be pre-characterized using a ratio measurement or other means, and those parameters fixed to the pre-characterized values during normal measurements. After such pre-characterization, only the contaminant layer on the reference pieces and properties of the unknown sample would be treated as unknowns in multiple ratio measurements. A further generalization might treat multiple contaminant layers, due to different types of photodeposited contaminants, or to distinguish the effects of photocontaminants from airborne molecular contaminants, which are known to absorb on wafer surfaces in normal fab environments.

An experiment demonstrating the effectiveness of the disclosed method consisted of 5 SiON samples, each measured at 5 measurement sites/wafer per day for 10 days. The measurement sites were slightly changed locally on the SiON samples each day to prevent photocontaminant buildup on the SiON samples themselves from affecting the results. The results for standard deviation of the 10 day measurements for each site are a metric of the stability for the SiON measurement. Photocontamination was allowed to occur on the two reference pieces. These conditions simulate the way the SiON process would be monitored in a fab production environment—i.e. each SiON sample would only be measured once, while the reference pieces would likely be used for many measurements, and consequently undergo the photocontamination process.

Each of the 250 measurements consists of 3 reflected intensities—one each from the two reference pads and one from the SiON measurement site. The data was first analyzed by calibrating $I_0$ using a dual pad calibration procedure with the two reference pads (similar to methods discussed in patent application Ser. Nos. 11/418,827, 11/418,846, and 11/789,686), and the thickness and percent nitrogen (via the EMA fraction) were analyzed using an EMA model and standard reflectance analysis. The 10-day standard deviation was computed for thickness and percent nitrogen for each site of each sample. The data was then recomputed using the multiple ratio analysis method described in this disclosure. The same optical models were used for reference and SiON materials for the recomputed data. The current method resulted in an average improvement in the 10-day standard deviation of approximately 37% for thickness and 26% for nitrogen percent.

In practice, similar stability enhancements can also be achieved through further optimization of the contaminant properties, or even alternate choices in calibration materials. The significance of this study lies in the fact that a stability enhancement was achieved using the disclosed method with the same reference pads, without further optimization of the reference or SiON material descriptions.

It is noted that the SiON description used for the analysis, in particular the oxide and nitride component optical properties, was generated using standard reflectance measurements by calibrating $I_0$. The good fit in FIGS. 13C and 13D are an indication that the previous analysis was largely successful. However, multiple SiON samples, each using a multiple ratio analysis, could be used to further refine the optical description of the SiON film, and consequently improve the fits in FIGS. 13C and 13D. In this case, the oxide and nitride component optical properties of the SiON film would be included as fit parameters, along with thickness and EMA fraction. The use of multiple SiON samples with different thicknesses helps to constrain the determination of the oxide and nitride component optical properties. This would likely result in even further improvement of stability results for both multiple ratio and calibrated reflectance measurements.

Figure 14:
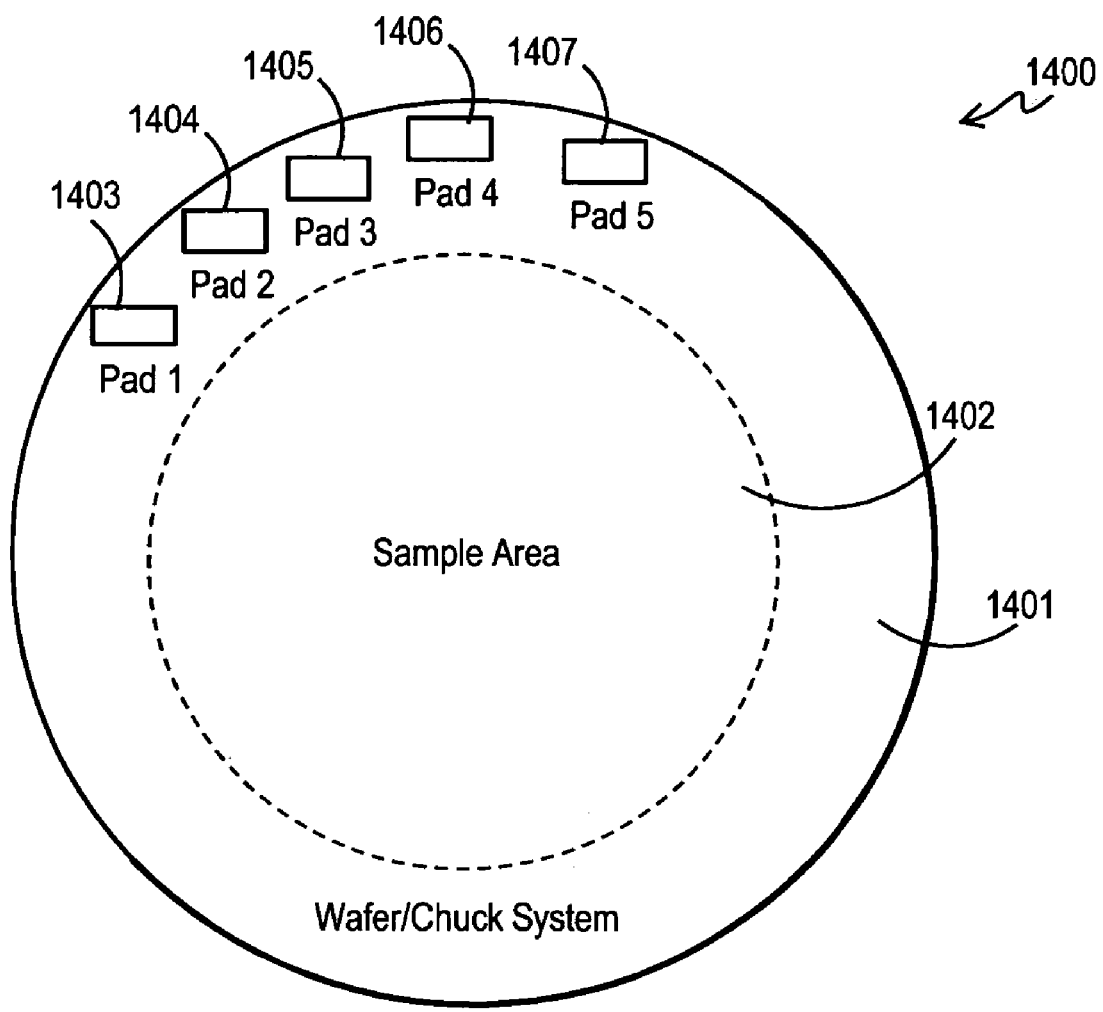
FIG. 14 illustrates a practical embodiment of the current invention including a moving stage with sample holder and several mounted reference pieces, each having distinct film structure.

As previously mentioned, one particularly attractive feature of the current method is that it may be combined with a multiple pad calibration procedure using the same or even additional reference pads on a single measurement platform. The multiple ratio method used may depend on the particular film measurement being done. In other words, whether or not to calibrate $I_0$ and generate reflectance or to use a multiple ratio calculation instead, or even which multiple ratio method to use, could be recipe dependent. FIG. 14 shows a generalized version of FIG. 3, where multiple reference pads, such as pad 1 1403, pad 2 1404, pad 3 1405, pad 4 1406, and pad 5 1407, each with different film characteristics are available for use depending on the sample being measured. The wafer/chuck system 1401 comprises a sample area 1402 similar to as described above. The intensities from any number of the reference pads could be used along with the sample intensity in any combination that does not depend on $I_0$ (not only limited to intensity ratios) and allows for accurate extraction of the desired sample parameters.

It is noted that the current method has been illustrated using a specific example, and one will recognize that many variations on the current procedure are possible, while still remaining within the scope of this disclosure. Additionally, the method described herein has been described for use with VUV reflectometer measurements, for which it is particularly advantageous, but the concept is valid for reflectance measurements carried out at any wavelength. The method described herein has also described a moving stage and sample holder, and can obviously be conceived to include automation via robotic wafer handling, fab interface software, and any number of other common modifications of optical metrology equipment for manufacturing environments.

Further modifications and alternative embodiments of the techniques disclosed herein will be apparent to those skilled in the art in view of this description. It will be recognized, therefore, that the techniques disclosed herein are not limited by these example arrangements. Accordingly, this description is to be construed as illustrative only and is for the purpose of teaching those skilled in the art the manner of carrying out the techniques disclosed herein. It is to be understood that the forms of the techniques disclosed herein shown and described are to be taken as the presently preferred embodiments. Various changes may be made in the implementations and architectures. For example, equivalent elements may be substituted for those illustrated and described herein, and certain features of the techniques disclosed herein may be utilized independently of the use of other features, all as would be apparent to one skilled in the art after having the benefit of this description of the techniques disclosed herein.

What is claimed is:

1. A method of measuring properties of a sample under test, comprising:
providing a reflectometer and at least one reference sample, which is separate from the sample under test, wherein the at least one reference sample is unstable under conditions in which the reflectometer is operated due to a buildup of a contaminant layer on the at least one reference sample during operation of the reflectometer;
collecting a set of data from the sample under test and at least one reference sample; and
utilizing a combination of the sample under test and reference sample data that is independent of incident intensity to determine a property of the sample under test, without calibrating incident reflectometer intensity.

2. The method of claim 1, wherein the data obtained from the sample under test and the at least one reference sample includes intensity data.

3. The method of claim 2, wherein reflectance ratios are obtained from the intensity data.

4. The method of claim 3, wherein one or more properties of the sample under test are obtained by analyzing reflectance ratios using thin film models and a regression analysis to determine one or more properties of one or more of the sample under test and the at least one reference sample.

5. The method of claim 2, wherein the collecting a set of data from the sample under test and at least one reference sample comprises collecting a set of data from the sample under test and a plurality of reference samples.

6. The method of claim 5, wherein plurality of reference samples comprises at least a first and second reference sample wherein the first reference sample comprises a relatively thick $SiO_2/Si$ film structure and the second reference sample comprises a native $SiO_2/Si$ film structure.

7. A method of measuring properties of a sample under test, comprising:
providing a reflectometer and at least one reference sample, wherein the at least one reference sample is unstable under conditions in which the reflectometer is operated;
collecting a set of data from the sample under test and at least one reference sample; and
utilizing a combination of the sample under test and reference sample data that is independent of incident intensity to determine a property of the sample under test, without calibrating incident reflectometer intensity,
wherein the data obtained from the sample under test and the at least one reference sample includes intensity data,
wherein the collecting a set of data from the sample under test and at least one reference sample comprises collecting a set of data from the sample under test and a plurality of reference samples, and
wherein the reflectance ratios comprise at least one ratio with data from the relatively thick $SiO_2/Si$ film structure in the numerator and data from the sample under test in the denominator and another ratio with data from the relatively thick $SiO_2/Si$ film structure in the numerator and data from the native $SiO_2/Si$ film structure in the denominator.

8. The method of claim 5, wherein the contaminant layer is included in a model for the reference samples.

9. The method of claim 5, wherein the sample under test is an ultra-thin silicon oxynitride or hafnium-silicide film.

10. The method of claim 1, wherein the reflectometer is operated in at least vacuum ultraviolet (VUV) wavelengths and the at least one reference sample is unstable under VUV conditions.

11. The method of claim 10, wherein the data obtained from the sample under test and the at least one reference sample includes intensity data.

12. The method of claim 11, wherein reflectance ratios are obtained from the intensity data.

13. The method of claim 12, wherein one or more properties of the sample under test are obtained by analyzing reflectance ratios using thin film models and a regression analysis to determine one or more properties of one or more of the sample under test and the at least one reference sample.

14. The method of claim 11, wherein the collecting a set of data from the sample under test and at least one reference sample comprises collecting a set of data from the sample under test and a plurality of reference samples.

15. A system for measuring properties of a sample under test, comprising:
at least one reference sample, which is separate from the sample under test;
a reflectometer configured for collecting a set of data from the sample under test and the at least one reference sample wherein the at least one reference sample is unstable under conditions in which the reflectometer is operated due to a buildup of a contaminant layer on the at least one reference sample during operation of the reflectometer; and a computer operating a software routine configured to utilize a combination of the sample under test and reference sample data that is independent of incident intensity to determine a property of the sample under test, without calibrating incident reflectometer intensity.

16. The system of claim 15, wherein the at least one reference sample is a reference piece integrated with a sample holding system.

17. The system of claim 16, further comprising of a plurality of the reference pieces.

18. The system of claim 15, wherein the data obtained from the sample under test and the at least one reference sample includes intensity data and wherein the software routine is configured to obtain reflectance ratios from the intensity data.

19. The system of claim 15, wherein the at least one reference sample comprises a plurality of reference samples.

20. The system of claim 19, wherein the plurality of reference samples comprises at least a first and second reference sample wherein the first reference sample comprises a relatively thick $SiO_2$/Si film structure and the second reference sample comprises a native $SiO_2$/Si film structure.

21. The system of claim 15, wherein the reflectometer is configured to operate in at least vacuum ultraviolet (VUV) wavelengths and the at least one reference sample is unstable under VUV conditions.

22. The system of claim 21, wherein the at least one reference sample is a reference piece integrated with a sample holding system.

23. The system of claim 22, further comprising of a plurality of the reference pieces.

24. The system of claim 21, wherein the data obtained from the sample under test and the at least one reference sample includes intensity data and wherein the software routine is configured to obtain reflectance ratios from the intensity data.

25. The system of claim 21, wherein the at least one reference sample comprises a plurality of reference samples.

26. A system for measuring properties of a sample under test, comprising:

at least one reference sample;

a reflectometer, configured for collecting a set of data from the sample under test and the at least one reference sample wherein the at least one reference sample is unstable under conditions in which the reflectometer is operated; and a computer operating a software routine that selectably operates in at least one of a plurality of measurement modes, the plurality of measurement modes including at least a first measurement mode and a second measurement mode, wherein, the first measurement mode is configured to utilize a combination of the sample under test and reference sample data that is independent of incident intensity to determine a property of the sample under test, without calibrating incident reflectometer intensity, and the second measurement mode is configured to utilize the reference sample data in a manner that is independent of incident intensity to determine one or more properties of one or more reference pieces, thereby determining the incident intensity of the reflectometer, after which reflectance of samples under test is determinable.

27. The system of claim 26, wherein the at least one reference sample is a reference piece integrated with a sample holding system.

28. The system of claim 27, further comprising of a plurality of the reference pieces.

29. The system of claim 26, wherein in the first measurement mode the data obtained from the sample under test and the at least one reference sample includes intensity data and wherein the software routine is configured to obtain reflectance ratios from the intensity data.

30. The system of claim 26, wherein in at least the first measurement mode the at least one reference sample comprises a plurality of reference samples.

31. The system of claim 30, wherein in the first measurement mode the plurality of reference samples comprises at least a first and second reference sample wherein the first reference sample comprises a relatively thick $SiO_2$/Si film structure and the second reference sample comprises a native $SiO_2$/Si film structure.

32. A method of measuring properties of a sample under test, comprising:

providing a reflectometer and at least one reference sample, wherein the at least one reference sample is unstable under conditions in which the reflectometer is operated;

collecting a set of data from the sample under test and at least one reference sample; and selectably operating the system in at least one of a plurality of measurement modes, the plurality of measurement modes including at least a first measurement mode and a second measurement mode, wherein, the first measurement mode is configured to utilize a combination of the sample under test and reference sample data that is independent of incident intensity to determine a property of the sample under test, without calibrating incident reflectometer intensity, and the second measurement mode is configured to utilize the reference sample data in a manner that is independent of incident intensity to determine one or more properties of one or more reference pieces, thereby determining the incident intensity of the reflectometer, after which reflectance of samples under test is determinable.

33. The method of claim 32, wherein in the first measurement mode the data obtained from the sample under test and the at least one reference sample includes intensity data.

34. The method of claim 33, wherein in the first measurement mode reflectance ratios are obtained from the intensity data.

35. The method of claim 34, where the reflectance ratios comprise at least one ratio with data from the relatively thick $SiO_2$/Si film structure in the numerator and data from the sample under test in the denominator and another ratio with data from the relatively thick $SiO_2$/Si film structure in the numerator and data from the native $SiO_2$/Si film structure in the denominator.

36. The method of claim 32, wherein in the first measurement mode one or more properties of the sample under test are obtained by analyzing reflectance ratios using thin film models and a regression analysis to determine one or more properties of one or more of the sample under test and the at least one reference sample.

37. The method of claim 32, wherein the collecting a set of data from the sample under test and at least one reference sample comprises collecting a set of data from the sample under test and a plurality of reference samples.

38. The method of claim 32, wherein the at least one reference sample comprises at least a first and second reference sample wherein the first reference sample comprises a relatively thick $SiO_2$/Si film structure and the second reference sample comprises a native $SiO_2$/Si film structure.

39. The method of claim 32, where a contaminant layer is included in a model for the reference samples.

* * * * *